(12) United States Patent
Nakatsugawa et al.

(10) Patent No.: US 8,471,212 B2
(45) Date of Patent: Jun. 25, 2013

(54) RADIOGRAPHY DEVICE

(71) Applicant: FUJIFILM Corporation, Tokyo (JP)

(72) Inventors: Haruyasu Nakatsugawa, Kanagawa-ken (JP); Naoyuki Nishino, Kanagawa-ken (JP); Yasunori Ohta, Kanagawa-ken (JP); Naoto Iwakiri, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/755,652

(22) Filed: Jan. 31, 2013

(65) Prior Publication Data
US 2013/0134316 A1    May 30, 2013

Related U.S. Application Data

(63) Continuation of application No. PCT/JP2011/064398, filed on Jun. 23, 2011.

(30) Foreign Application Priority Data

Aug. 31, 2010  (JP) ................................. 2010-194941

(51) Int. Cl.
*G01T 1/20*    (2006.01)

(52) U.S. Cl.
USPC .......................................................... 250/366

(58) Field of Classification Search
USPC .......................................................... 250/366
See application file for complete search history.

(56) References Cited

U.S. PATENT DOCUMENTS

| | | | |
|---|---|---|---|
| 5,047,624 A * | 9/1991 | Anno et al. | 250/214 VT |
| 2002/0014594 A1 | 2/2002 | Endo | |

FOREIGN PATENT DOCUMENTS

| JP | 2002-014168 A | 1/2002 |
|---|---|---|
| JP | 2005-114518 A | 4/2005 |
| JP | 2007-271504 A | 10/2007 |
| JP | 2009-068888 A | 4/2009 |

* cited by examiner

*Primary Examiner* — Kiho Kim
(74) *Attorney, Agent, or Firm* — Jean C. Edwards, Esq.; Edwards Neils PLLC

(57) ABSTRACT

In this radiography device, the radiation conversion panel side of a scintillator is formed in a convex shape towards the radiation conversion panel, the end portions of columnar crystals are formed at said side, and the end portions of the columnar crystals can contact the radiation conversion panel.

20 Claims, 16 Drawing Sheets

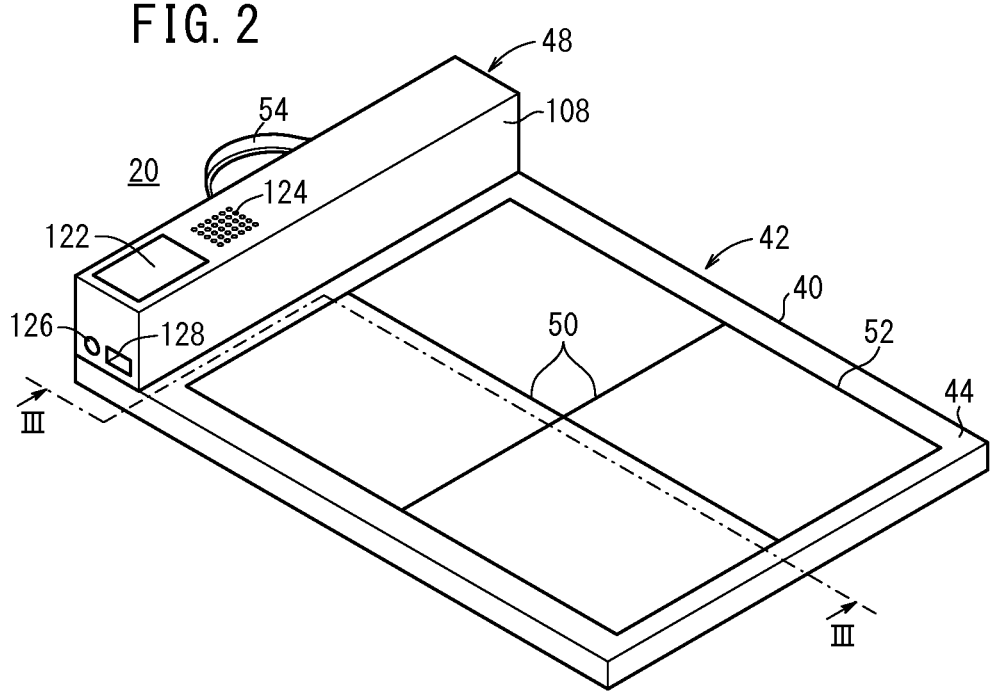

RADIOGRAPHY DEVICE

CROSS-REFERENCE TO RELATED APPLICATIONS AND PRIORITY CLAIM

This application is a Continuation of International Application No. PCT/JP2011/064398 filed on Jun. 23, 2011, which was published under PCT Article 21(2) in Japanese, which is based upon and claims the benefit of priority from Japanese Patent Application No. 2010-194941 filed on Aug. 31, 2010, the contents all of which are incorporated herein by reference.

TECHNICAL FIELD

The present invention relates to a radiographic image capturing apparatus (radiography device) having a scintillator for converting a radiation into a visible light and a radiation conversion panel for converting the visible light into an electric signal.

BACKGROUND ART

In the medical field, radiographic image capturing apparatuses have been widely used for detecting a radiation applied to a subject from a radiation source and passed through the subject to acquire a radiographic image of the subject. For example, the radiographic image capturing apparatus has an indirect conversion radiation detector containing a scintillator for converting the radiation transmitted through the subject into a visible light and a radiation conversion panel for converting the visible light into electric signals.

In a recently proposed radiation detector, the scintillator is formed by vapor-depositing columnar crystals of CsI or the like on a support board, the columnar crystals are approximately perpendicular to the support board, and the distal end portions of the columnar crystals are located on the radiation conversion panel with a protective layer interposed therebetween (see Japanese Laid-Open Patent Publication No. 2009-068888).

In a case where the radiation is converted into the visible light by the columnar crystals, the visible light passes through column portions of the columnar crystals, is transmitted from the distal end portions of the columnar crystals through the protective layer, and reaches the radiation conversion panel. Then, the incident visible light can be converted to the electric signal in the radiation conversion panel.

SUMMARY OF INVENTION

In Japanese Laid-Open Patent Publication No. 2009-068888, the radiographic image capturing apparatus, which has the radiation detector containing the scintillator, the protective layer, and the radiation conversion panel, is used while pressing the columnar crystals in the scintillator onto the radiation conversion panel via the protective layer. Thus, in Japanese Laid-Open Patent Publication No. 2009-068888, the scintillator and the radiation conversion panel cannot be frequently contacted with and separated from each other depending on the states of the radiographic image capturing apparatus.

For example, a doctor or a radiological technician may drop the radiographic image capturing apparatus by mistake during transport. In such a case, the radiographic image capturing apparatus is subjected to an external shock, and the columnar crystals are inadvertently subjected to a stress. Consequently, the columnar crystals may be broken (fractured) or cracked, resulting in deterioration in the performance of the radiographic image capturing apparatus such as radiographic image blurring, etc. In view of this problem, it is desirable that the scintillator and the radiation conversion panel can be separated from each other immediately before the external shock is applied to the radiographic image capturing apparatus (immediately before the inadvertent stress is applied to the columnar crystals). Furthermore, it is desirable that the radiographic image capturing apparatus is returned to the original state (the scintillator and the radiation conversion panel are brought into contact with each other) rapidly after a predetermined time has elapsed from the application of the external shock. The scintillator and the radiation conversion panel are desirably brought into contact with each other while avoiding the breakage (fracture) and cracking of the columnar crystals.

However, Japanese Laid-Open Patent Publication No. 2009-068888 describes no measures against the frequent contact and separation of the scintillator and the radiation conversion panel in the radiographic image capturing apparatus.

An object of the present invention is to prevent the cracking of the columnar crystals in the scintillator even if the scintillator and the radiation conversion panel are frequently contacted with and separated from each other in the radiographic image capturing apparatus.

In view of achieving the above object, according to the present invention, there is provided a radiographic image capturing apparatus comprising a radiation detector having a scintillator for converting a radiation into a visible light and a radiation conversion panel for converting the visible light into an electric signal, wherein the scintillator contains columnar crystals for converting the radiation into the visible light, the columnar crystals extend in non-parallel with the radiation conversion panel, the scintillator has a convex surface facing the radiation conversion panel, the distal end portions of the columnar crystals are disposed on the convex surface, and the distal end portions of the columnar crystals are capable of being brought into contact with the radiation conversion panel.

In the radiographic image capturing apparatus, the radiation detector preferably further has a buffer layer permeable to the visible light between the scintillator and the radiation conversion panel. It is desirable that the buffer layer has a first surface facing the scintillator and a second surface facing the radiation conversion panel, the first surface is capable of being brought into contact with the distal end portions of the columnar crystals, and the second surface is capable of being brought into contact with the radiation conversion panel.

In this case, the convex surface of the scintillator facing the radiation conversion panel may be convexly curved and protruded toward the radiation conversion panel. The first surface of the buffer layer may be curved along the convex surface of the scintillator and may be brought into contact with the distal end portions of the columnar crystals.

Alternatively, the convex surface of the scintillator facing the radiation conversion panel may be tapered toward the radiation conversion panel. The center of the convex surface may be approximately parallel to the radiation conversion panel, and the buffer layer may be brought into contact with the center of the convex surface. In this case, a light shielding layer may be disposed on a tapered portion of the convex surface of the scintillator to shield the visible light emitted from the distal end portions of the columnar crystals in the tapered portion.

The buffer layer is preferably a flexible plastic sheet, more specifically a transparent flexible plastic sheet permeable to the visible light such as a silicone rubber film, a polyimide film, a polyarylate film, a biaxially-oriented polystyrene film, or an aramid film. The thickness of the buffer layer is preferably less than 50 µm, more preferably less than 30 µm.

A surface of the radiation conversion panel, which is brought into contact with the second surface of the buffer layer, is preferably planarized using a tetrafluoroethylene resin film.

The columnar crystals are preferably cesium iodide crystals, and are preferably sealed by a protective moisture-proof material.

The bottoms of the columnar crystals may be disposed on a reflective film for reflecting the visible light (converted from the radiation by the columnar crystals) toward the buffer layer or a support board for supporting the scintillator and reflecting the visible light toward the buffer layer, the columnar crystals being vapor-deposited on the support board. In this case, the reflective film or the support board may act to seal the columnar crystals and may have a moisture-proof property.

In the invention, the radiation conversion panel may contain a flexible plastic sheet or a flexible thin glass sheet.

The radiographic image capturing apparatus preferably further has an image correction device for correcting a radiographic image corresponding to the electric signal read from the radiation conversion panel depending on the shape of the convex surface of the scintillator.

The radiographic image capturing apparatus may further have a contact mechanism for bringing the distal end portions of the columnar crystals into contact with the radiation conversion panel along the extending direction of the columnar crystals.

In this case, the contact mechanism may act to bring the distal end portions of the columnar crystals into contact with the radiation conversion panel at least when the radiation is emitted to the radiation detector.

The radiographic image capturing apparatus preferably further has a transfer detector and a contact control device. The transfer detector detects transfer of the radiographic image capturing apparatus. The contact control device controls the contact mechanism to bring the distal end portions of the columnar crystals into contact with the radiation conversion panel in a case where the radiation is emitted to the radiation detector. Furthermore, the contact control device controls the contact mechanism to stop the contact control between the distal end portions of the columnar crystals and the radiation conversion panel in a case where a physical quantity relevant to the transfer of the radiographic image capturing apparatus detected by the transfer detector becomes larger than a predetermined threshold value.

In this case, the contact control device controls the contact mechanism to bring the distal end portions of the columnar crystals into contact with the radiation conversion panel when a radiation source for emitting the radiation makes a preparation of the emission.

The contact mechanism is preferably an air-bag, which is inflated and deflated along the extending direction of the columnar crystals to control the contact between the distal end portions of the columnar crystals and the radiation conversion panel. The radiographic image capturing apparatus preferably further has an inflator for supplying an inert gas to the air-bag to inflate the air-bag along the extending direction of the columnar crystals.

As described above, in the present invention, the scintillator has the convex surface facing the radiation conversion panel. The distal end portions of the columnar crystals are located on the convex surface in the scintillator, and can be brought into contact with the radiation conversion panel.

Consequently, even if the scintillator containing the columnar crystals and the radiation conversion panel are frequently contacted with and separated from each other depending on the states of the radiographic image capturing apparatus, the columnar crystals can be prevented from being broken (fractured) and cracked.

In addition, since the scintillator has the convex surface facing the radiation conversion panel, even in a case where the scintillator and the radiation conversion panel are frequently contacted with and separated from each other, the columnar crystals can be prevented from being cracked in an end of the scintillator in the process of pressing the scintillator onto the radiation conversion panel.

BRIEF DESCRIPTION OF DRAWINGS

FIG. 2 is a perspective view of the electronic cassette shown in FIG. 1;

DESCRIPTION OF EMBODIMENTS

A preferred embodiment of the radiographic image capturing apparatus of the present invention will be described in detail below with reference to FIGS. 1 to 16B.

[Constitution of the Embodiment]

Figure 1:
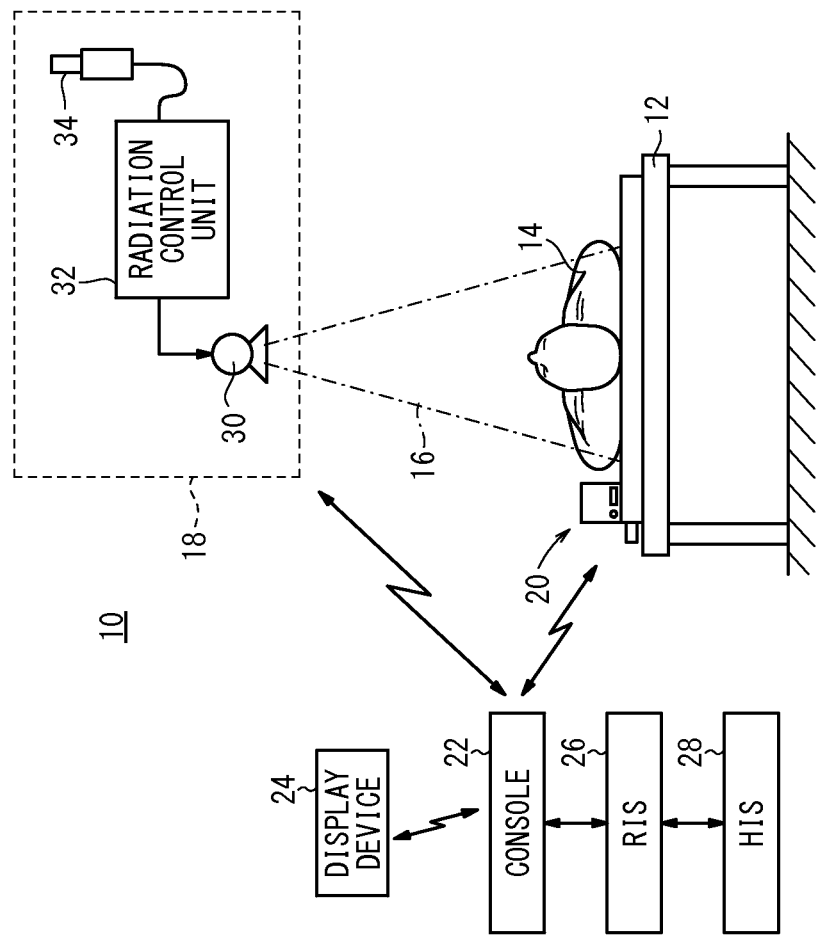
FIG. 1 is a schematic view of a radiographic image capturing system having a radiographic image capturing apparatus (electronic cassette) according to an embodiment of the present invention.

FIG. 1 is a schematic view of a radiographic image capturing system 10 having an electronic cassette 20 (radiographic image capturing apparatus) according to this embodiment.

The radiographic image capturing system 10 has a radiation output apparatus 18 for applying a radiation 16 to a subject 14 such as a patient lying on an image capturing base 12 such as a bed, the electronic cassette 20 for detecting the radiation 16 that has passed through the subject 14 and converting the detected radiation 16 into a radiographic image, a console 22 for controlling the entire radiographic image capturing system 10 and receiving operation input by a doctor or a radiological technician (hereinafter referred to simply as the doctor), and a display device 24 for displaying the captured radiographic image and the like.

The radiation output apparatus 18, the electronic cassette 20, the console 22, and the display device 24 may send signals to and receive signals from each other via wireless communication using UWB (Ultra Wide Band), wireless LAN according to IEEE 802.11.a/b/g/n standard or the like, millimeter waves, etc. Alternatively, the components may send and receive signals via wired communication using cables.

The console 22 is connected to a radiology information system (RIS) 26, which generally manages radiographic images and other information handled in the radiological department of a hospital. The RIS 26 is connected to a hospital information system (HIS) 28, which generally manages medical information in the hospital.

The radiation output apparatus 18 has a radiation source 30 for emitting the radiation 16, a radiation control unit 32 for controlling the radiation source 30, and a radiation switch 34. The radiation source 30 applies the radiation 16 to the electronic cassette 20. The radiation 16 emitted from the radiation source 30 may be X-ray, α-ray, β-ray, γ-ray, electron beam, or the like. The radiation switch 34 is of a two stage stroke type. When the radiation switch 34 is pressed halfway by the doctor, the radiation control unit 32 makes a preparation to emit the radiation 16. When the radiation switch 34 is pressed completely, the radiation 16 is emitted from the radiation source 30.

As described above, the radiation output apparatus 18, the electronic cassette 20, the console 22, and the display device 24 can send signals to and receive signals from each other. Therefore, when the radiation switch 34 is pressed halfway, the radiation output apparatus 18 may send a signal indicating the preparation for the emission to the console 22, etc. Then, when the radiation switch 34 is pressed completely, the radiation output apparatus 18 may send a signal indicating the start of the emission of the radiation 16 to the console 22, etc.

Figure 3A:
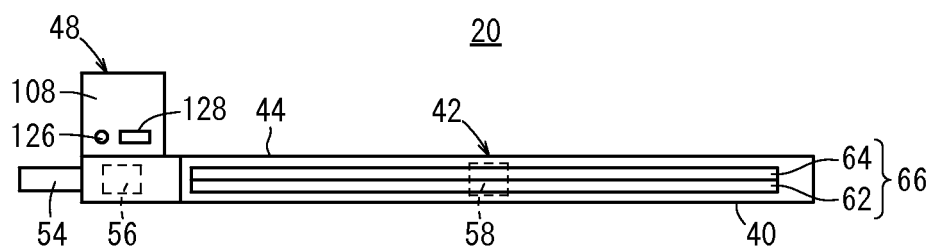
FIGS. 3A and 3B are cross-sectional views of the electronic cassette taken along the line III-III of FIG. 2.
Figure 3B:
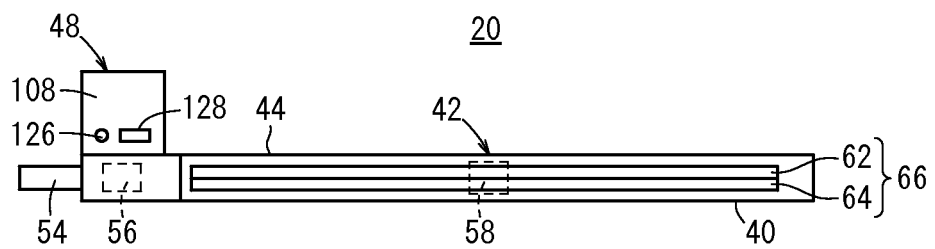

FIG. 2 is a perspective view of the electronic cassette 20 shown in FIG. 1, and FIGS. 3A and 3B are cross-sectional views of the electronic cassette 20 taken along the line III-III of FIG. 2.

The electronic cassette 20 has a panel unit 42 and a control unit 48 disposed thereon. The panel unit 42 is thinner than the control unit 48.

The panel unit 42 has a substantially rectangular casing 40 composed of a material permeable to the radiation 16. The front surface (upper surface) of the panel unit 42 serves as an exposed surface 44 to be irradiated with the radiation 16. The exposed surface 44 has guide lines 50 substantially at the center as a reference for the image capturing range and position of the subject 14. The outer frame of the guide lines 50 corresponds to an image capturable area 52 indicative of an irradiation field of the radiation 16. The central position of the guide lines 50 (the crisscross intersection between the guide lines 50) corresponds to the center of the image capturable area 52.

A handle 54, which the doctor can grip, is attached to the side surface of the casing 40 where the control unit 48 is disposed. The doctor can grip the handle 54 to transport the electronic cassette 20 to a desired place (e.g. the image capturing base 12). Thus, the electronic cassette 20 is a transportable radiographic image capturing apparatus.

A three-axis acceleration sensor 56 (transfer detector) for detecting an acceleration (the three-axis components thereof) of the electronic cassette 20 is disposed in the casing 40 in the vicinity of the handle 54. The acceleration sensor 56 is located in the vicinity of the handle 54 in order that the acceleration sensor 56 can be prevented from being broken due to a drop impact in a case where the electronic cassette 20 is dropped by mistake. Furthermore, a three-axis pressure sensor 58 (transfer detector) for detecting an external pressure (the three-axis components thereof) applied to the electronic cassette 20 is disposed in the casing 40 in the vicinity of the center of the guide lines 50. When the electronic cassette 20 is moved, the acceleration is produced. When the pressure is applied to the electronic cassette 20, the electronic cassette 20 may be displaced. Therefore, the physical quantities are relevant to the transfer of the electronic cassette 20.

Figure 10:
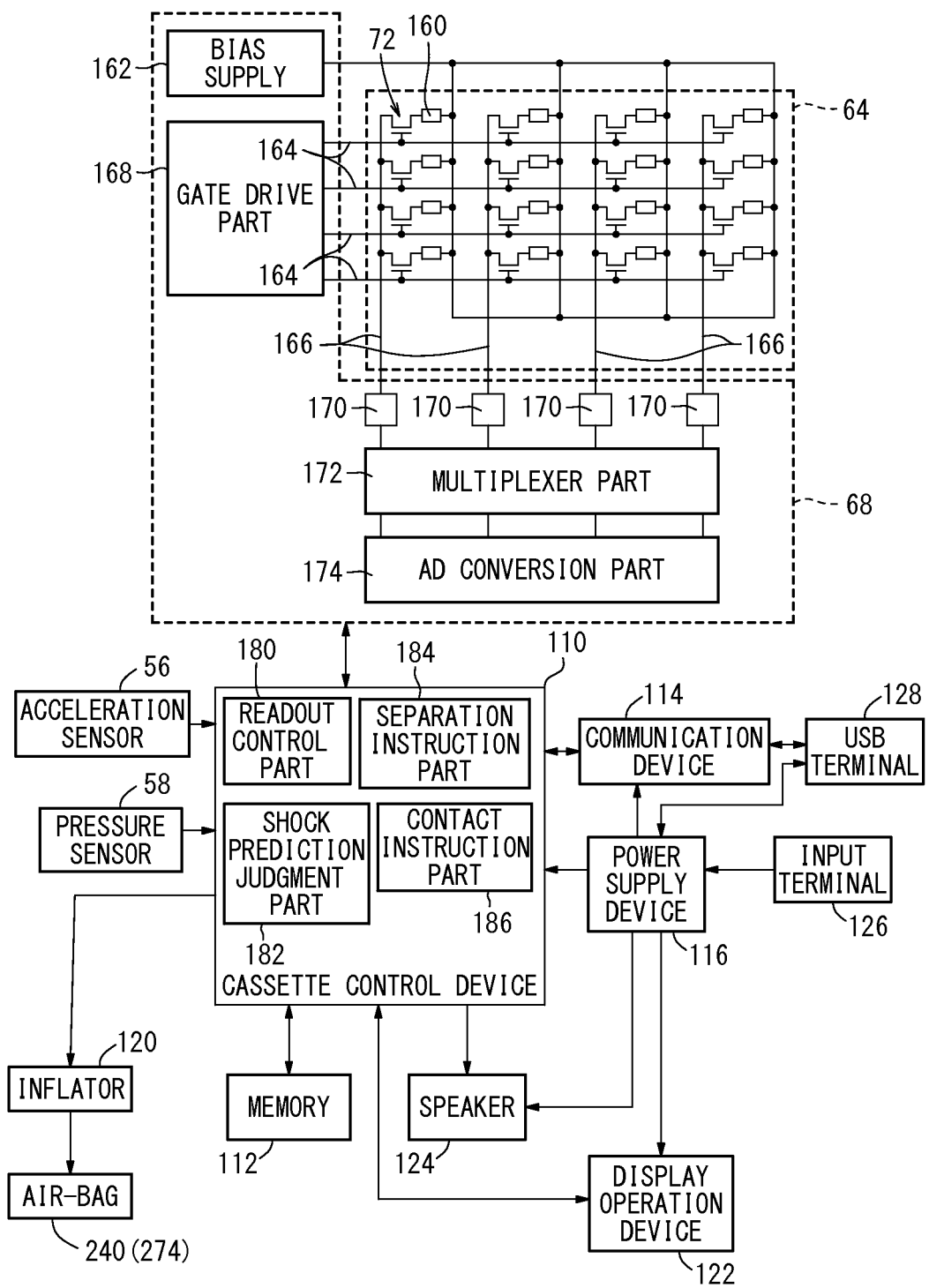
FIG. 10 is a schematic structural view of the electric structure of the electronic cassette of FIG. 1.

A radiation detector 66 containing a scintillator panel 62 and a radiation conversion panel 64, and further a drive circuit device 68 for driving the radiation conversion panel 64 are provided in the casing 40 (see FIG. 10).

Figure 4A:
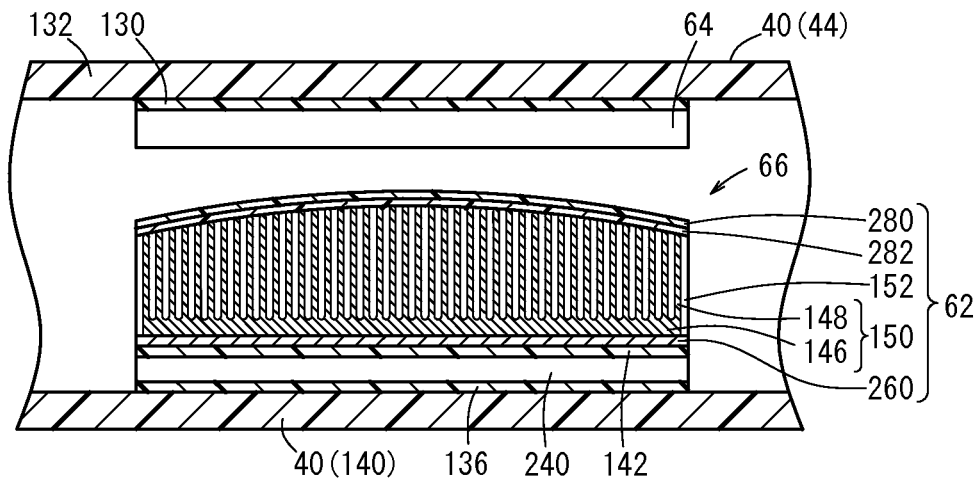
FIGS. 4A and 4B are cross-sectional views of an example of a principal part in the vicinity of a radiation detector in the electronic cassette of FIG. 2.
Figure 4B:
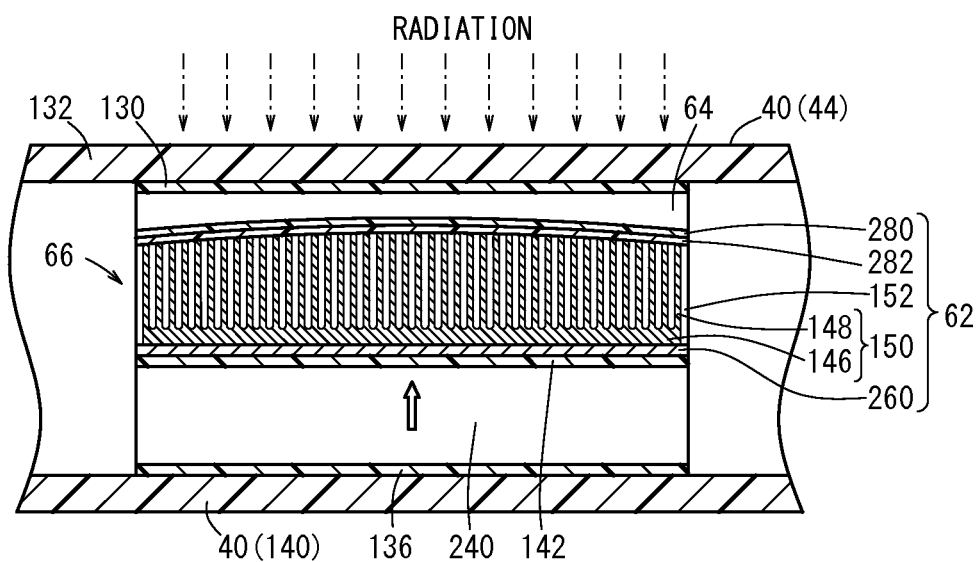

The scintillator panel 62 contains a scintillator 150 for converting the radiation 16 transmitted through the subject 14 into a visible fluorescent light (see FIGS. 4A and 4B). The radiation conversion panel 64 is an indirect conversion type panel, which can transmit the radiation 16 and can convert the fluorescence from the scintillator 150 into an electric signal.

The radiation detector 66 of FIG. 3A is a face side reading type, i.e. ISS (Irradiation Side Sampling) type radiation detector, wherein the radiation conversion panel 64 and the scintillator panel 62 are arranged in the casing 40 in this order from the exposed surface 44 to be irradiated with the radiation 16. The radiation detector 66 of FIG. 3B is a reverse side reading type, i.e. PSS (Penetration Side Sampling) type radiation detector, wherein the scintillator panel 62 and the radiation conversion panel 64 are arranged in the casing 40 in this order from the exposed surface 44 to be irradiated with the radiation 16.

The control unit 48 has a substantially rectangular casing 108 composed of a material impermeable to the radiation 16. The casing 108 extends along one side of the exposed surface 44, and the control unit 48 is located outside of the image capturable area 52 on the exposed surface 44. In this case, the casing 108 contains a cassette control device 110 (contact control device, image correction device) for controlling the panel unit 42, a buffer memory 112 for storing captured radiographic image data, a communication device 114 for sending signals to and receiving signals from the console 22 through a wireless communication link, and a power supply device 116 such as a battery (see FIG. 10). The power supply device 116 supplies electric power to the components in the electronic cassette 20.

A touch panel type display operation device 122 capable of displaying the captured radiographic image and the like, into which the doctor can input various information, and a speaker 124 for outputting a sound indicating various information to the doctor are disposed on the upper surface of the casing 108.

Furthermore, an AC adapter input terminal 126 for charging the power supply device 116 from an external power supply and a USB terminal 128 as an interface for sending information to and receiving information from an external device (such as the console 22) are disposed on a side surface of the casing 108.

FIGS. 4A and 4B are cross-sectional views of a principal part of the radiation detector 66 in the casing 40. An example of the ISS type radiation detector 66 of FIG. 3A is shown in the drawings. In this case, the radiation detector 66 is located between a top plate 132 on the exposed surface 44 and a bottom plate 140 on the bottom surface of the casing 40.

Specifically, an air-bag 240 (contact mechanism) is bonded to the bottom plate 140 by an adhesive layer 136, and the scintillator panel 62 is bonded to the air-bag 240 by an adhesive layer 142. The radiation conversion panel 64 is bonded to the top plate 132 (the surface facing the bottom plate 140) by the adhesive layer 130.

The scintillator panel 62 contains the scintillator 150.

The scintillator 150 is provided such that a thallium-doped cesium iodide (CsI:Tl) or the like is vacuum-deposited onto a surface of a support board (not shown) to form a strip-like columnar crystal structure 148. A non-columnar crystal portion 146 is formed on the surface of the support board in the proximal end portion of the scintillator 150. In the columnar crystal structure 148, columns are arranged at a certain distance and extend in a direction non-parallel to the support board, ideally in a direction substantially perpendicular to the support board (the vertical direction at 90° of FIGS. 4A and 4B). The non-columnar crystal portion 146 in the scintillator 150 approximately flatly extends along the surface of the support board. The top of the columnar crystal structure 148 is convexly curved at the center. Thus, the thickness of the scintillator 150 varies with position. The columnar crystal structure 148 is insufficient in moisture resistance, and the non-columnar crystal portion 146 is significantly poor in moisture resistance. Therefore, the CsI scintillator 150 is sealed by a protective moisture-proof material 152.

The scintillator panel 62 having the scintillator 150 is incorporated in the casing 40 as follows.

First, the scintillator 150 is separated from the support board. In this process, the substantially flat non-columnar crystal portion 146 is not covered with the protective moisture-proof material 152. Therefore, a reflective film 260 composed of Al or the like is formed on the non-columnar crystal portion 146. The reflective film 260 reflects a fluorescent light converted from the radiation 16 by the columnar crystal structure 148 toward the distal end portion of the columnar crystal structure 148. The reflective film 260 has a fluorescent light reflective property and a moisture-proof property, and acts to seal the columnar crystal structure 148 and the non-columnar crystal portion 146 in cooperation with the protective moisture-proof material 152.

A buffer layer 280 composed of a flexible plastic sheet is bonded by an adhesive layer 282 to the distal end portion of the columnar crystal structure 148 in the protective moisture-proof material 152.

The buffer layer 280 is preferably a flexible transparent plastic sheet permeable to the fluorescent light, such as a silicone rubber film, a polyimide film, a polyarylate film, a biaxially-oriented polystyrene film, or an aramid film. In this case, the thickness of the buffer layer 280 is preferably less than 50 μm, more preferably less than 30 μm.

As shown in FIG. 4A, the scintillator panel 62 having the above-described structure is incorporated in the casing 40 such that the reflective film 260 faces downward (the air-bag 240) and the buffer layer 280 faces upward (the radiation conversion panel 64). Therefore, in the scintillator panel 62, the reflective film 260 is bonded to the air-bag 240 by the adhesive layer 142.

The columnar crystal structure 148 is hard and brittle, and thereby is insufficient in resistance to external pressure or stress. Therefore, in a case where the electronic cassette 20 is dropped or subjected to an excessive external pressure, the columnar crystal structure 148 may be broken (fractured) or cracked. As a result, the image capturing performance and the sensitivity of the electronic cassette 20 may be deteriorated, resulting in radiographic image blurring, etc.

More specifically, in the columnar crystal structure 148 in the scintillator 150, the columns have to be arranged at a certain distance (e.g. at a filling rate of 70% to 85%) to prevent the reduction of the fluorescent light and the crosstalk of the fluorescent lights between the columns. Thus, for example, in a case where the doctor drops the electronic cassette 20 by mistake during transport, the electronic cassette 20 is subjected to an external shock, and the columnar crystal structure 148 is inadvertently subjected to a stress, so that the columnar crystal structure 148 may be broken (fractured) or cracked to deteriorate the performance of the electronic cassette 20, resulting in the radiographic image blurring, etc. Also in a case where the subject 14 comes into contact with the exposed surface 44 and applies an excessive pressure to the electronic cassette 20 through the exposed surface 44, the columnar crystal structure 148 is inadvertently subjected to a stress, so that the columnar crystal structure 148 may be broken (fractured) or cracked.

The scintillator 150 and the radiation conversion panel 64 may be fixed (the columnar crystal structure 148 and the radiation conversion panel 64 may be pressed to each other) by using a protective layer, an adhesive layer, or the like. In this case, when the columnar crystal structure 148 is displaced on the radiation conversion panel 64 due to an external shock, the surface of the radiation conversion panel 64 may be scratched, and an image defect may be generated in the radiographic image by the scratch.

In general, as described in Japanese Laid-Open Patent Publication No. 2009-068888, the electronic cassette 20 is used while pressing the scintillator 150 onto the radiation conversion panel 64 through the protective layer. Therefore, the scintillator 150 and the radiation conversion panel 64 are not frequently contacted with and separated from each other depending on the states of the electronic cassette 20.

Thus, it is desirable that the scintillator 150 and the radiation conversion panel 64 can be separated from each other immediately before the external shock is applied to the electronic cassette 20 (the inadvertent stress is applied to the columnar crystal structure 148). Furthermore, it is desirable that the electronic cassette 20 can be returned to the original state (the scintillator 150 and the radiation conversion panel 64 can be brought into contact with each other) rapidly after a predetermined time has elapsed from the application of the external shock. The scintillator 150 and the radiation conversion panel 64 are desirably brought into contact with each other while avoiding the breakage (fracture) and cracking of the columnar crystal structure 148.

As described above, the columnar crystal structure 148 is hard and brittle, and thereby is insufficient in the resistance to external pressure or stress. Both sides of the scintillator 150 may be fixed by a support board 144 and the radiation conversion panel 64 using an adhesive agent (adhesive layer) or the like respectively. In this case, if the support board 144, the scintillator 150, and the radiation conversion panel 64 have different thermal expansion coefficients, as schematically shown in FIGS. 9A and 9B, as in a bimetal, the entire radiation detector 66 is warped toward the support board 144 and the scintillator 150 or the radiation conversion panel 64 due to temperature change.

Figure 9A:
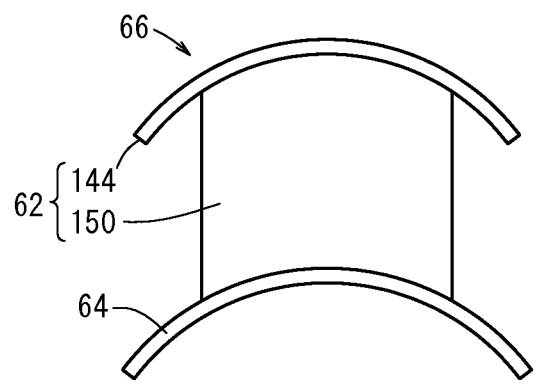
FIGS. 9A and 9B are explanatory views for illustrating a problem arises in a case where a scintillator and a radiation conversion panel are bonded by an adhesive layer.
Figure 9B:
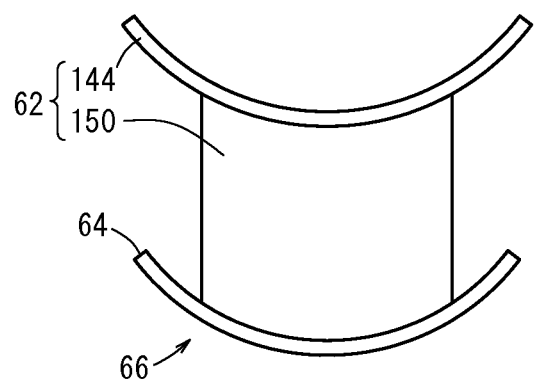

Assuming that the radiation conversion panel 64 is composed of a glass substrate (approximately 3 ppm/° C.) and the support board 144 is composed of aluminum (approximately 30 ppm/° C.), the shapes of the radiation conversion panel 64, the scintillator 150, and the support board 144 are changed due to the temperature change as schematically shown in FIGS. 9A and 9B. At a relatively high temperature (for example, 50° C.) of FIG. 9A and a relatively low temperature (for example, −20° C.) of FIG. 9B, the radiation conversion panel 64, the scintillator 150, and the support board 144 are significantly warped due to the extremely different thermal expansion coefficients.

The support board 144, the scintillator 150, and the radiation conversion panel 64 may have the same thermal expansion coefficient (may be composed of the same material) to prevent the warpage. However, in this case, the selection of the support board 144 is restricted.

In a case where the radiation conversion panel 64 and the scintillator 150 are bonded by the adhesive layer, the distance between the scintillator 150 and the radiation conversion panel 64 is increased due to the thickness of the adhesive layer. Therefore, the adhesive layer may lead to the radiographic image blur.

Furthermore, the adhesive layer may be deteriorated (the adhesive agent in the adhesive layer may be colored) by the radiation 16, so that the light transmittance of the adhesive layer may be lowered. In this case, also the visible light sensitivity of the radiation conversion panel 64 is lowered.

In addition, both of the scintillator 150 having the columnar crystal structure 148 and the radiation conversion panel 64 are expensive components for the electronic cassette 20. In the case where the scintillator 150 and the radiation conversion panel 64 are bonded by the adhesive layer, in a case where one of the components is broken or crashed, also the other component having the normal function is discarded. Thus, the bonding of the scintillator 150 and the radiation conversion panel 64 by the adhesive layer results in poor reworkability in view of reusing the normal component.

Accordingly, in this embodiment, the scintillator 150 having the columnar crystal structure 148 and the radiation conversion panel 64 can be frequently contacted and separated in the electronic cassette 20 while preventing the cracking of the columnar crystal structure 148. The scintillator 150 and the radiation conversion panel 64 can be brought into contact with each other without using the adhesive agent (the adhesive layer).

Specifically, as shown in FIGS. 4A and 4B, the air-bag 240 is bonded to the bottom plate 140 of the casing 40 by the adhesive layer 136, and the scintillator panel 62 is bonded to the air-bag 240 by the adhesive layer 142. The air-bag 240 is connected to an inflator 120 as shown in FIG. 10. The air-bag 240 and the inflator 120 have common structures for automotive air-bags and inflators. The top of the columnar crystal structure 148 is convexly curved at the center, and one surface (first surface) of the buffer layer 280 is bonded to the curved surface by the adhesive layer 282. Therefore, the buffer layer 280 is convexly curved and protruded toward the radiation conversion panel 64. The radiation conversion panel 64 preferably contains a flexible plastic substrate such as a polyimide film, a polyarylate film, a biaxially-oriented polystyrene film, or an aramid film.

In the process of capturing the radiographic image of the subject 14, the inflator 120 acts to ignite an ignition agent (not shown), generate an inert gas such as a nitrogen or helium gas, and send the generated inert gas to the air-bag 240. When the inert gas is sent from the inflator 120, the air-bag 240 is inflated toward the radiation conversion panel 64 due to the gas pressure. Thus, the scintillator panel 62 is shifted toward the radiation conversion panel 64, and the other surface (second surface) of the buffer layer 280, which is not bonded to the scintillator 150, is pressed onto the radiation conversion panel 64 as shown in FIG. 4B. Consequently, the relative positions of the scintillator 150 and the radiation conversion panel 64 are fixed in the casing 40.

In this case, the top of the buffer layer 280 and the columnar crystal structure 148 is convexly curved and protruded toward the radiation conversion panel 64, and the radiation conversion panel 64 is composed of the flexible plastic substrate. Therefore, in a case where the second surface of the buffer layer 280 is pressed onto the surface of the radiation conversion panel 64, the surface of the radiation conversion panel 64 is slightly concaved along the second surface of the buffer layer 280. Thus, the contact of the buffer layer 280 and the radiation conversion panel 64 can be improved. Consequently, the scintillator 150 and the radiation conversion panel 64 can be appropriately brought into (tight) contact with each other using the buffer layer 280 interposed therebetween without the adhesive agent. It is preferred that the inert gas is sent from the inflator 120 to gradually inflate the air-bag 240 from the viewpoint of not damaging the buffer layer 280 and the radiation conversion panel 64 in the contact step.

In a case where the radiation conversion panel 64 contains a thick glass substrate and is hardly to be deformed (is not flexible) as shown in FIG. 4B, a silicone rubber may be used for the buffer layer 280. In this case, when the scintillator 150 having the buffer layer 280 and the radiation conversion panel 64 are brought into contact with each other, the center of the buffer layer 280 is thinned, and the columnar crystal structure 148 and the radiation conversion panel 64 are appropriately tightly contacted at the center. Furthermore, since the center of the buffer layer 280 is thinned, the distance between the columnar crystal structure 148 and the radiation conversion panel 64 is reduced at the center, whereby the image blurring is reduced in the center of the image capturable area 52, which is important for capturing the image of the subject 14. The advantageous effects can be easily obtained by controlling the force to press the scintillator 150 onto the radiation conversion panel 64.

The buffer layer 280 (the scintillator 150) and the radiation conversion panel 64 can be in (tight) contact with each other in this manner. In this state, when the radiation 16 is transmitted through the radiation conversion panel 64 and the buffer layer 280 and reaches the scintillator 150, the radiation 16 is converted into the visible fluorescent light by the columnar crystal structure 148, the converted fluorescent light is introduced from the columns in the columnar crystal structure 148 through the buffer layer 280 to the radiation conversion panel 64, and thus the fluorescent light can be converted into the electric signal by the radiation conversion panel 64. In this case, though part of the fluorescent light may be emitted toward the reflective film 260, the part can be reflected by the reflective film 260 and the non-columnar crystal portion 146 toward the buffer layer 280 and may be introduced into the radiation conversion panel 64.

The radiation conversion panel 64 is formed by stacking a pixel (photoelectric conversion element) for converting the fluorescent light into the electric signal on the above-described flexible plastic substrate (TFT substrate). The surface of the radiation conversion panel 64, facing the support board 144, is planarized with a tetrafluoroethylene resin film. In this case, the photoelectric conversion element may contain an organic photoconductor (OPC) for absorbing the fluorescent light and generating the electric charge. A part (TFT 72) for reading the electric charge from the photoelectric conversion element may contain an amorphous IGZO (a-IGZO). The photoelectric conversion element and the TFT 72 using the OPC and the a-IGZO can be formed on the plastic substrate at a relatively low temperature.

After the radiographic image is obtained, the supply of the inert gas from the inflator 120 to the air-bag 240 is stopped, and the inert gas in the air-bag 240 is discharged from a discharge hole (not shown). Thus, the buffer layer 280 and the radiation conversion panel 64 can be separated by deflating the air-bag 240.

In this manner, at least when the radiation 16 is emitted without the external shock (drop or pressure shock), the buffer layer 280 and the radiation conversion panel 64 are pressed onto each other (brought into contact with each other) to fix the relative positions of the scintillator 150 and the radiation conversion panel 64 in the casing 40 (see FIG. 4B). Of course, the scintillator 150 and the radiation conversion panel 64 may be contacted even if the doctor transports the electronic cassette 20 without dropping.

In a case where the external shock is applied to the electronic cassette 20 while the buffer layer 280 and the radiation conversion panel 64 are in contact with each other (e.g., in a case where the doctor drops the electronic cassette 20 by mistake during transport, and the acceleration value detected by the acceleration sensor 56 becomes larger than a predetermined threshold value, or in a case where the subject 14 violently comes into contact with the exposed surface 44 in the step of positioning the subject 14 on the exposed surface 44 or the like, the excessive pressure is applied to the electronic cassette 20, and the pressure value detected by the pressure sensor 58 becomes larger than a predetermined threshold value), the inadvertent stress is applied to the columnar crystal structure 148 due to the drop or pressure shock, whereby the columnar crystal structure 148 may be broken (fractured) or cracked, and the columnar crystal structure 148 may be displaced on the radiation conversion panel 64 to scratch the surface of the radiation conversion panel 64.

In such a case, the inflator 120 stops the supply of the inert gas, and the inert gas in the air-bag 240 is discharged from the discharge hole. Thus, the air-bag 240 is deflated and shrunk in the thicknesswise direction of the casing 40 (toward the bottom plate 140), so that the buffer layer 280 and the scintillator 150 can be separated from the radiation conversion panel 64 as shown in FIG. 4A. Consequently, even if the inadvertent stress is applied to the scintillator 150 due to the drop of the electronic cassette 20 or the application of the excessive pressure, the breakage (fracture) and cracking of the columnar crystal structure 148 and the surface scratching of the radiation conversion panel 64 can be prevented.

The above-described predetermined threshold value is an acceleration value smaller than a gravitational acceleration value observed when the doctor drops the electronic cassette 20 on a floor or the like by mistake during transport. Alternatively, the predetermined threshold value is a pressure value smaller than a measured pressure value leading to the breakage (fracture) and cracking of the columnar crystal structure 148 and the surface scratching of the radiation conversion panel 64 in the electronic cassette 20 subjected to the pressure. Thus, when the detected acceleration or pressure value becomes larger than the threshold value, the columnar crystal structure 148 may be broken or cracked, and the radiation conversion panel 64 may be scratched. Therefore, in this embodiment, immediately before that, the inflator 120 is stopped and the inert gas in the air-bag 240 is discharged, whereby the scintillator 150 and the buffer layer 280 is separated from the radiation conversion panel 64 to appropriately protect the scintillator 150 against the drop or pressure shock.

In this embodiment, the external pressure to be applied to the electronic cassette 20 may be predicted from the product of the acceleration of the electronic cassette 20 and the time. In a case where the electronic cassette 20 falls for a long time, even though the acceleration of the electronic cassette 20 does not reach the free fall acceleration (gravitational acceleration), the drop velocity of the electronic cassette 20 is increased. Therefore, the electronic cassette 20 is expected to be subjected to a remarkably high shock pressure. Specifically, in a case where the doctor grips the handle 54 and swings the electronic cassette 20 in an arc around the handle 54 (e.g. the doctor slides the electronic cassette 20 on the image capturing base 12 and separates the electronic cassette 20 from the image capturing base 12), the doctor may hit a part of the electronic cassette 20 against the image capturing base 12, so that the electronic cassette 20 may be subjected to a large impact. In this embodiment, the scintillator 150 can be appropriately protected against such an impact.

In this embodiment, the shock to be applied to the electronic cassette 20 may be evaluated based on an image capturing procedure for the subject 14 (e.g. a procedure in the lying or standing position) and the acceleration of the electronic cassette 20. For example, in a case where an image of the subject 14 in the lying position is captured using the electronic cassette 20 on the image capturing base 12, and then the electronic cassette 20 is transferred from the image capturing base 12, the user may drop the electronic cassette 20 from the image capturing base 12 onto the floor. In this case, the scintillator 150 and the buffer layer 280 may be separated from the radiation conversion panel 64 when the free fall acceleration is detected by the acceleration sensor 56 after the image capturing process.

In the process of capturing an image of the subject 14 in the standing position, an image capturing base (not shown) is located in a relatively high position, and the electronic cassette 20 is attached to the image capturing base. Therefore, the scintillator 150 and the buffer layer 280 may be separated from the radiation conversion panel 64 in a case where the electronic cassette 20 is removed from the image capturing base and the free fall acceleration is detected by the acceleration sensor 56 after the image capturing process.

In such an image capturing procedure that the electronic cassette 20 may be dropped before or after the image capturing process, the scintillator 150 and the buffer layer 280 may be preliminarily separated from the radiation conversion panel 64 by stopping the inflator 120 and the air-bag 240. The scintillator 150 and the buffer layer 280 may be pressed onto the radiation conversion panel 64 in a case where the electronic cassette 20 is placed on the image capturing base 12 (or the non-illustrated image capturing base for the image capturing process in the standing position).

Though the scintillator 150 and the buffer layer 280 are completely separated from the radiation conversion panel 64 in the above description, this embodiment is not limited thereto. The scintillator 150 and the buffer layer 280 may be in contact with the radiation conversion panel 64 even if the air-bag 240 is stopped, as long as the contact pressure observed when the air-bag 240 is stopped is approximately zero or lower than the pressure observed when the scintillator 150 and the buffer layer 280 are pressed onto the radiation conversion panel 64. Thus, in this embodiment, when the inflator 120 and the air-bag 240 are stopped, at least the contact control of the scintillator 150 and the buffer layer 280 with the radiation conversion panel 64 (the pressing of the scintillator 150 and the buffer layer 280 onto the radiation conversion panel 64) is stopped.

Figure 5A:
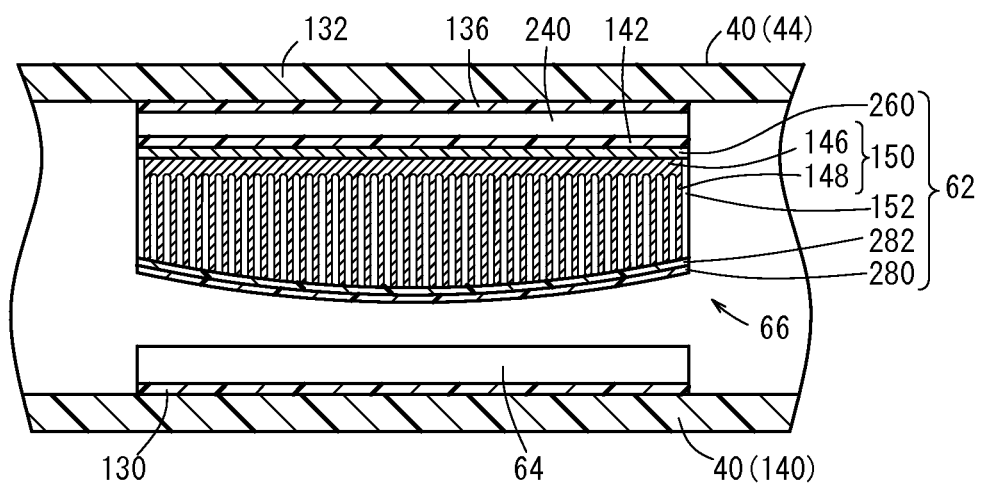
FIGS. 5A and 5B are cross-sectional views of another example of the principal part in the vicinity of the radiation detector in the electronic cassette of FIG. 2.
Figure 5B:
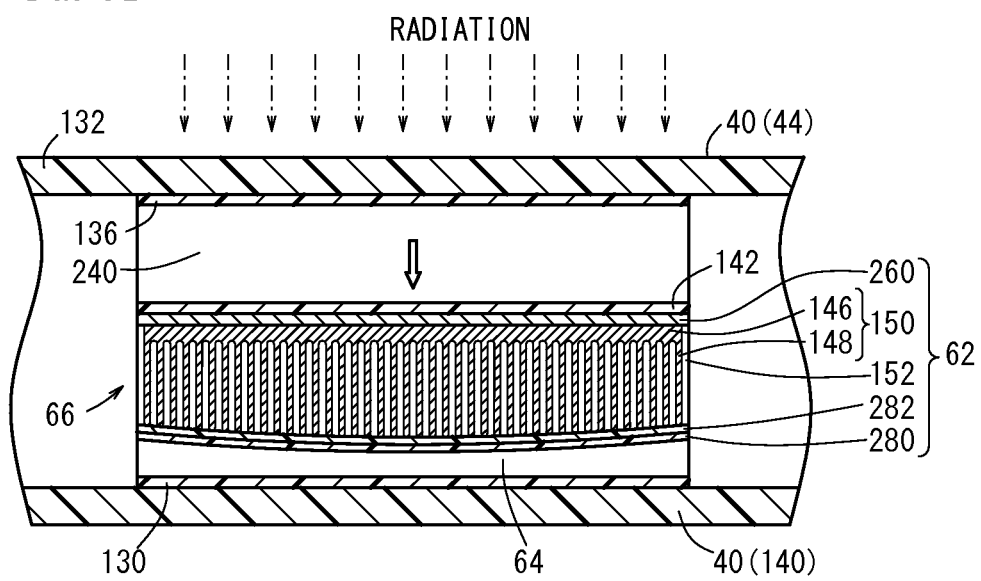

FIGS. 5A and 5B are cross-sectional detail views of the PSS type radiation detector 66 shown in FIG. 3B. Similarly to the ISS type radiation detector 66 of FIGS. 4A and 4B, the PSS type radiation detector 66 is capable of inflating the air-bag 240 toward the radiation conversion panel 64 to bring the buffer layer 280 and the radiation conversion panel 64 into contact with each other.

Figure 6A:
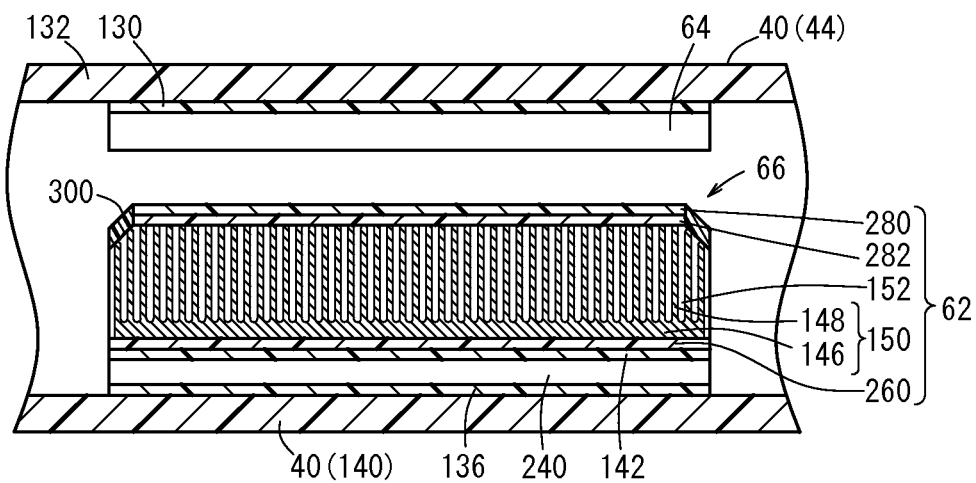
FIGS. 6A and 6B are cross-sectional views of a further example of the principal part in the vicinity of the radiation detector in the electronic cassette of FIG. 2.
Figure 6B:
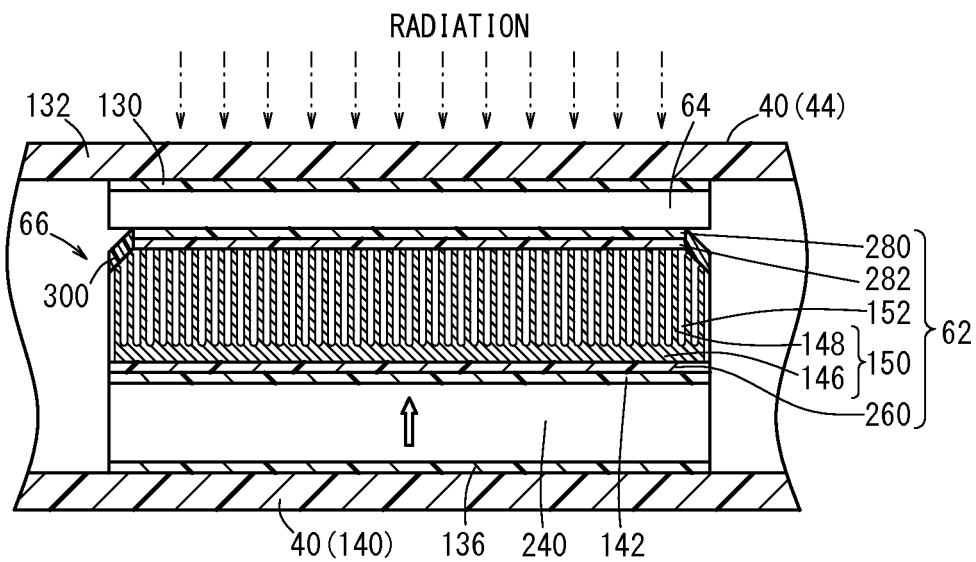

In FIGS. 6A and 6B, the distal end portion of the columnar crystal structure 148 in the protective moisture-proof material 152 is tapered toward the radiation conversion panel 64, the center of the distal end portion is approximately parallel to the radiation conversion panel 64, and the buffer layer 280 is bonded to the center by the adhesive layer 282. In this case, the buffer layer 280 is approximately parallel to the radiation conversion panel 64. Therefore, as shown in FIG. 6B, the buffer layer 280 and the radiation conversion panel 64 can be brought into (tight) contact with each other without deforming the radiation conversion panel 64. When the columnar crystal structure 148 and the buffer layer 280 are pressed onto the radiation conversion panel 64, the periphery of the scintillator 150 (the tapered portion) is not pressed against the radiation conversion panel 64. Therefore, the breakage and cracking can be prevented in the periphery. Furthermore, a light shielding layer 300 for preventing the visible light from leaking from the tapered portion of the distal end portion of the columnar crystal structure 148 is formed on the tapered portion of the protective moisture-proof material 152. In the radiation conversion panel 64, a portion facing to the light shielding layer 300 is preferably outside the radiographic image capturing range.

Figure 7A:
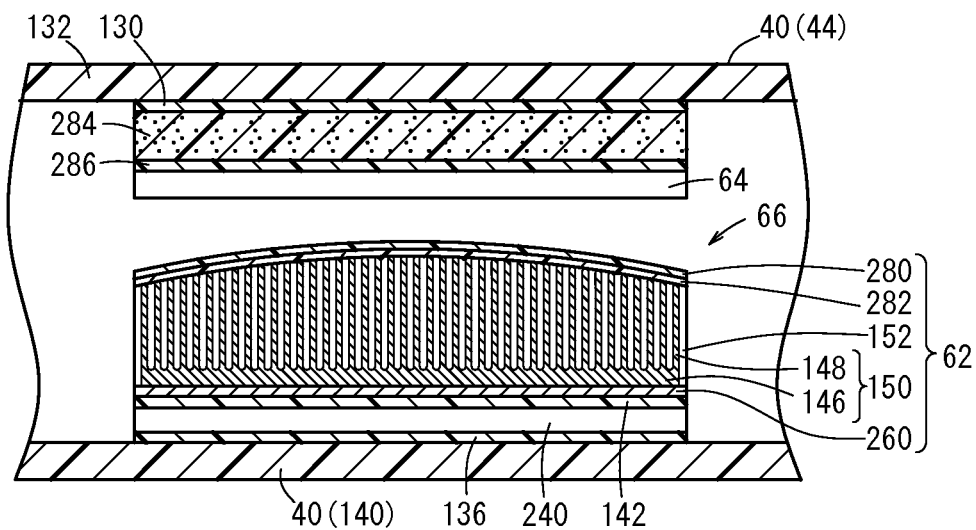
FIGS. 7A and 7B are cross-sectional views of a still further example of the principal part in the vicinity of the radiation detector in the electronic cassette of FIG. 2.
Figure 7B:
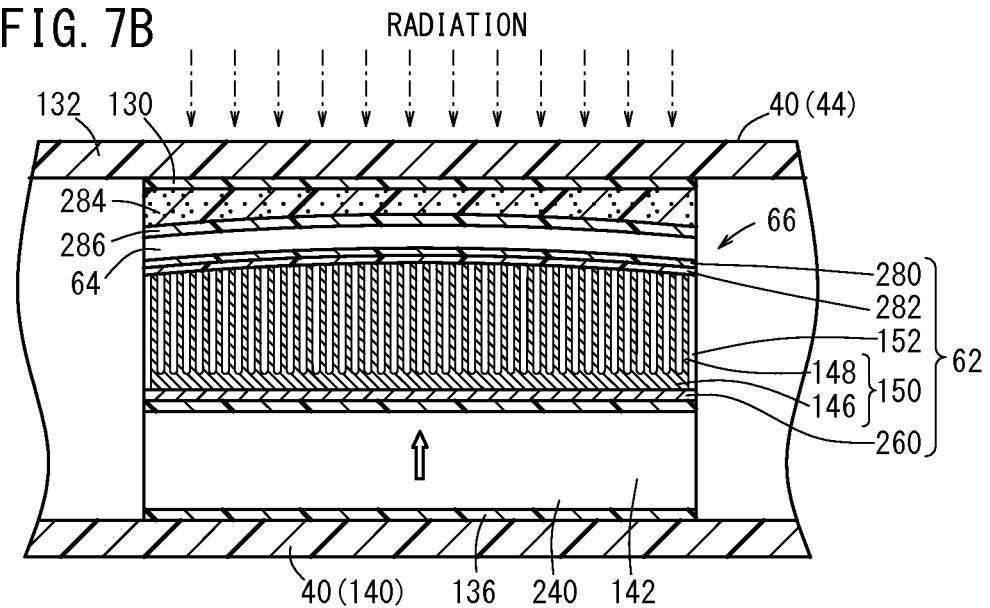

In this embodiment, the TFT substrate in the radiation conversion panel 64 is not limited to the above-described thin flexible plastic substrate, and may be a thin flexible glass substrate. The radiation conversion panel 64 containing the flexible thin glass substrate is shown in FIGS. 7A and 7B. A sponge 284 is bonded to the top plate 132 by the adhesive layer 130, and the radiation conversion panel 64 is bonded to the sponge 284 by an adhesive layer 286. In this case, when the buffer layer 280 is pressed onto the radiation conversion panel 64, the sponge 284 and the radiation conversion panel 64 are concaved to be brought into tight contact with the convexly curved surface of the buffer layer 280. Therefore, the buffer layer 280 and the radiation conversion panel 64 can be appropriately brought into contact with each other (see FIG. 7B). In a case where the buffer layer 280 and the radiation conversion panel 64 are separated from each other, the radiation conversion panel 64 can be readily returned to the original shape by the sponge 284 as shown in FIG. 7A.

Figure 8A:
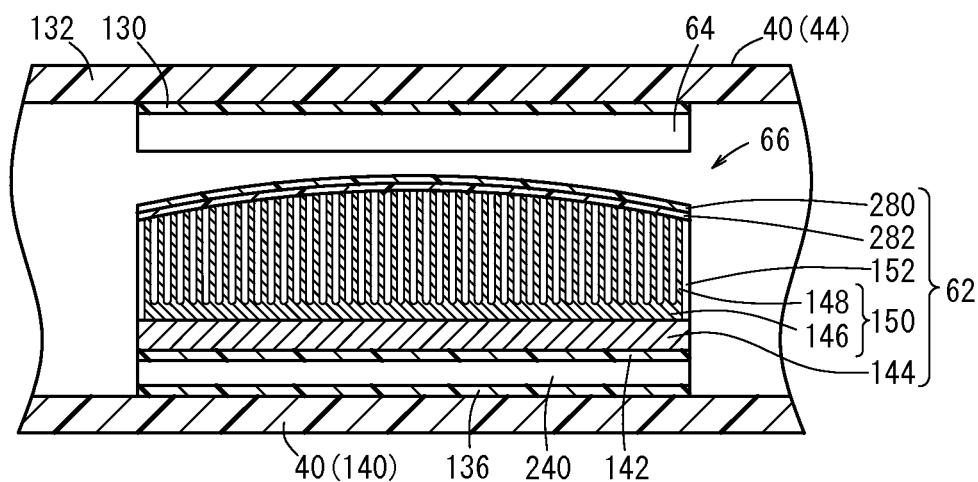
FIGS. 8A and 8B are cross-sectional views of a still further example of the principal part in the vicinity of the radiation detector in the electronic cassette of FIG. 2.
Figure 8B:
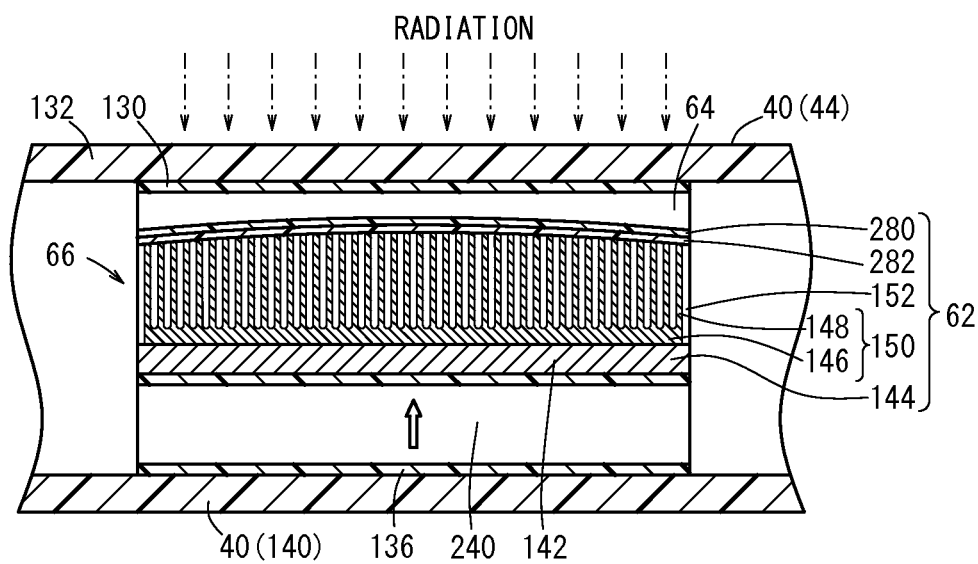

In the above description, the scintillator 150 is separated from the support board to prepare the scintillator panel 62. However, in this embodiment, as shown in FIGS. 8A and 8B, the support board 144 of Al or the like having the vapor-deposited scintillator 150 may be used for the scintillator panel 62 without removing the support board 144 from the scintillator 150. In this case, the support board 144 can act as the reflective film 260, and the buffer layer 280 and the radiation conversion panel 64 can be contacted and separated similarly to those of FIGS. 4A and 4B.

In this embodiment, the buffer layer 280 and the radiation conversion panel 64 can be contacted and separated. Therefore, even if the support board 144 and the scintillator 150 are integrated, the above-described shape change of the scintillator 150 due to the temperature change can be prevented.

FIG. 10 is a schematic structural view of the electric structure of the electronic cassette 20 shown in FIG. 1.

The electronic cassette 20 has the structure containing pixels 160 disposed on the TFTs 72 arranged in a matrix. The pixels 160 are arranged in a matrix and each have a photoelectric conversion element (not shown). The pixels 160, which are supplied with a bias voltage from a bias supply 162 in the drive circuit device 68, store electric charges generated by photoelectric conversion of the visible light (fluorescent light). The TFTs 72 are turned on sequentially column by column, whereby the electric charge signals (electric signals) can be read from signal lines 166 as analog pixel signal values. Though the pixels 160 and the TFTs 72 are arranged vertically and horizontally in a 4×4 matrix in FIG. 10 for the sake of convenience, of course they may be arranged in a desired matrix.

The TFTs 72, connected to the pixels 160, are connected with gate lines 164 extending in the row direction and the signal lines 166 extending in the column direction. The gate lines 164 are connected to a gate drive part 168 in the drive circuit device 68, and the signal lines 166 are connected to a multiplexer part 172 in the drive circuit device 68 through charge amplifiers 170. The multiplexer part 172 is connected to an AD conversion part 174 for converting the analog electric signals into digital electric signals. The AD conversion part 174 outputs the converted digital electric signals (digital pixel signal values, hereinafter referred to also as digital values) to the cassette control device 110.

The cassette control device 110 is for controlling the entire electronic cassette 20. In this case, an information processor such as a computer can be used as the cassette control device 110 by installing a predetermined program thereinto.

In the cassette control device 110, the electric signals (the digital pixel signal values) are read from the radiation conversion panel 64 by a readout control part 180, and the radiographic image of the electric signals is corrected depending on the shape of the distal end portion of the columnar crystal structure 148 (protruded toward the radiation conversion panel 64).

The cassette control device 110 is connected with the memory 112 and the communication device 114. The memory 112 stores the digital pixel signal values after the image correction processing in the cassette control device 110, and the communication device 114 sends signals to and receives signals from the console 22. The communication device 114 sends to the console 22 a packet of one image (one-frame image) containing the pixel values arranged in a matrix. The power supply device 116 supplies electric power to the cassette control device 110, the memory 112, the communication device 114, etc. The electric power is transferred from the cassette control device 110 to the bias supply 162, and is supplied to the pixels 160 by the bias supply 108.

The cassette control device 110 has the readout control part 180, a shock prediction judgment part 182, a separation instruction part 184, and a contact instruction part 186.

The readout control part 180 controls the gate drive part 168, the charge amplifiers 170, the multiplexer part 172, and the AD conversion part 174, to read the electric signals stored in the pixels 160 sequentially row by row.

The shock prediction judgment part 182 judges whether or not the acceleration value detected by the acceleration sensor 56 or the pressure value detected by the pressure sensor 58 is larger or not than the predetermined threshold value. Thus, the shock prediction judgment part 182 acts to judge (predict), based on the result value detected by the acceleration sensor 56 or the pressure sensor 58, whether or not the external shock to be applied to the electronic cassette 20 due to the crash (drop) of the electronic cassette 20 against the floor or the excessive pressure on the electronic cassette 20 causes the breakage (fracture) or cracking of the columnar crystal structure 148 or the surface scratch of the radiation conversion panel 64.

In a case where the acceleration value detected by the acceleration sensor 56 or the pressure value detected by the pressure sensor 58 becomes larger than the threshold value, the shock prediction judgment part 182 sends a communication signal, which indicates that the external shock causing the breakage (fracture) or cracking of the columnar crystal structure 148 or the surface scratch of the radiation conversion panel 64 will be applied to the electronic cassette 20, to the separation instruction part 184.

The acceleration sensor 56 successively detects the acceleration and successively sends detection signals indicating the detected acceleration values to the cassette control device 110. The pressure sensor 58 successively detects the pressure and successively sends detection signals indicating the detected pressure values to the cassette control device 110. Thus, after the communication signal is sent to the separation instruction part 184, the shock prediction judgment part 182 then judges whether the acceleration value detected by the acceleration sensor 56 or the pressure value detected by the pressure sensor 58 becomes smaller or not than the threshold value. In a case where the acceleration value and the pressure value are smaller than the threshold values, the shock prediction judgment part 182 sends a communication signal, which indicates that the external shock is no longer likely to be applied to the electronic cassette 20, to the contact instruction part 186.

In a case where m represents the total weight of the electronic cassette 20, h represents the distance between the electronic cassette 20 and the floor at the start of the drop (the drop distance), g represents the gravitational acceleration, v represents the drop velocity of the electronic cassette 20 at the timing of the drop (crash) against the floor, and t represents the drop time from the drop start to the crash against the floor, the drop velocity v and the drop time t are obtained using the equations of $v=(2 \times g \times h)^{1/2}$ and $t=(2 \times h/g)^{1/2}$ respectively.

Instead of predicting and judging the shock using the acceleration value, the shock prediction judgment part 182 uses a predetermined time shorter than the drop time t as a threshold value. In this case, the time when the acceleration value detected by the acceleration sensor 56 is increased from approximately 0 to a predetermined level value corresponding to the drop of the electronic cassette 20 is considered as the drop start. The shock prediction judgment part 182 sends the communication signal to the separation instruction part 184 when the predetermined time of the threshold value has elapsed from the drop start. Thus, the shock prediction judgment part 182 predicts the crash by measuring the elapsed time from the drop start based on the acceleration value detected by the acceleration sensor 56. Therefore, also the measured elapsed time is the physical quantity relevant to the transfer of the electronic cassette 20.

When the communication signal is input from the shock prediction judgment part 182, the contact instruction part 186 sends, to the inflator 120, an operation start instruction signal for driving the air-bag 240. When the operation start instruction signal is entered, the inflator 120 ignites the ignition agent to generate the inert gas and sends the inert gas to the air-bag 240. On the other hand, when the communication signal is input from the shock prediction judgment part 182, the separation instruction part 184 sends, to the inflator 120, an operation stop instruction signal for stopping the inflator 120. When the operation stop instruction signal is entered, the inflator 120 stops the supply of the inert gas to the air-bag 240.

As described above, when the radiation switch 34 is pressed halfway by the doctor, the radiation control unit 32 sends the signal indicating the preparation for the emission of the radiation 16 to the console 22 via the wireless communication. In this case, the console 22 sends, to the electronic cassette 20 via the wireless communication, a synchronization control signal for synchronizing with the emission of the radiation 16 from the radiation source 30. When the electronic cassette 20 receives the synchronization control signal, the contact instruction part 186 sends the operation start instruction signal to the inflator 120 based on the synchronization control signal. Then, the inflator 120 starts to supply the inert gas to the air-bag 240 based on the operation start instruction signal. Consequently, the buffer layer 280 and the radiation conversion panel 64 are brought into contact with each other, so that the electronic cassette 20 becomes capable of detecting the radiation 16. Also when the doctor operates the display operation device 122 and thereby instructs to bring the buffer layer 280 and the radiation conversion panel 64 into contact with each other in the preparation stage for the image capturing process, the contact instruction part 186 can send the operation start instruction signal to the inflator 120.

On the other hand, when the doctor operates the display operation device 122 and thereby instructs to separate the buffer layer 280 and the radiation conversion panel 64 from each other after the radiographic image capturing process, the separation instruction part 184 can send the operation stop instruction signal to the inflator 120 to stop the inert gas supply from the inflator 120 to the air-bag 240.

[Operations of the Embodiment]

The radiographic image capturing system 10, which has the electronic cassette 20 of this embodiment, is basically constructed as described above. Operations of the radiographic image capturing system 10 will be described below with reference to the flowcharts of FIGS. 11 and 12.

The basic operation of the radiographic image capturing system 10 will be described first with reference to FIG. 11.

Figure 12:
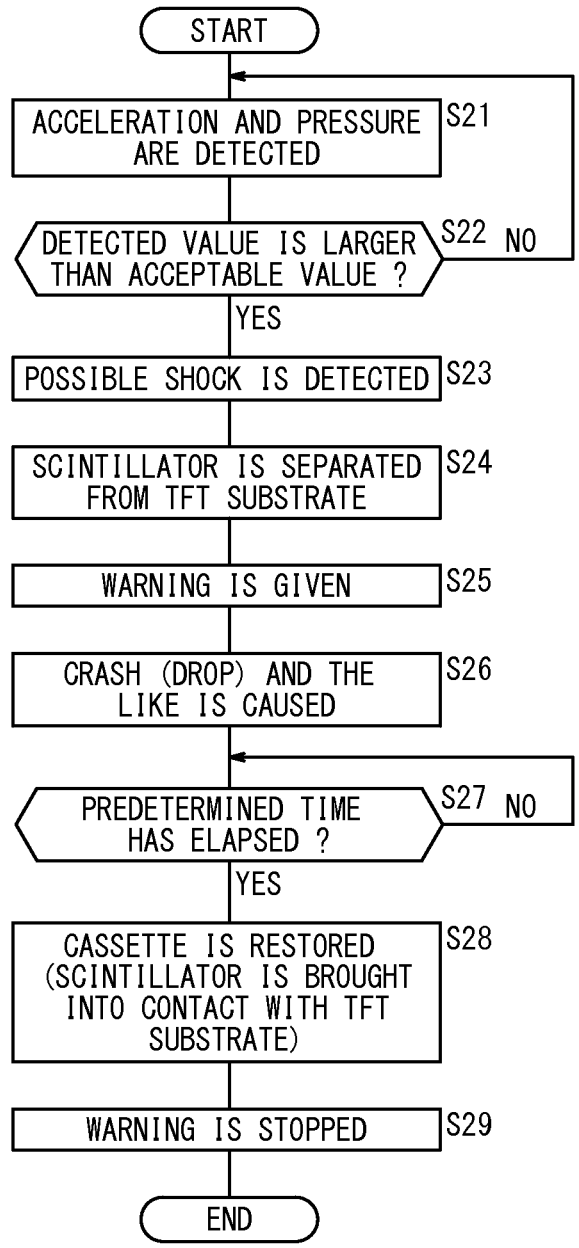
FIG. 12 is a flowchart of the operation of the radiographic image capturing system of FIG. 1 in a case where the electronic cassette is subjected to an external shock.

Then, the operation of the electronic cassette 20, in the case where the electronic cassette 20 is subjected to the external shock, will be described with reference to FIG. 12. Specifically, the operation of the components (the inflator 120 and the air-bag 240) in the electronic cassette 20, in the case where the doctor drops the electronic cassette 20 by mistake during transport or where the subject 14 violently comes into contact with the exposed surface 44 and applies the excessive pressure to the electronic cassette 20 in the step of positioning the subject 14, will be described.

Figure 11:
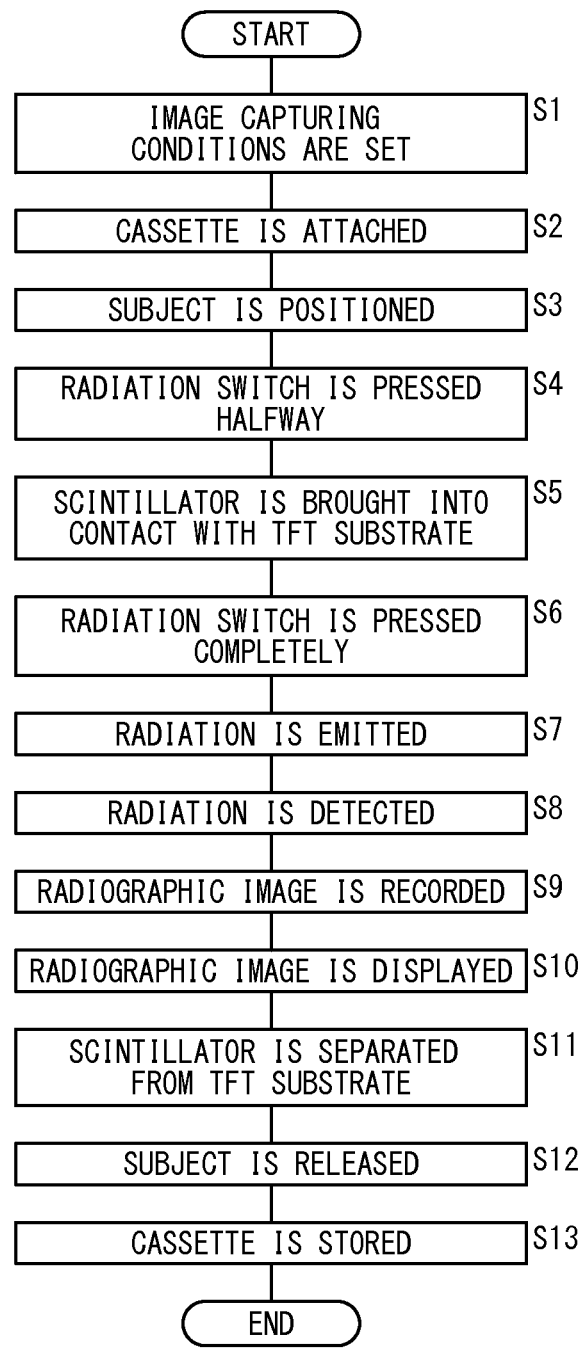
FIG. 11 is a flowchart of the operation of the radiographic image capturing system of FIG. 1.

In step S1 of FIG. 11, the doctor sets image capturing conditions for the subject 14 based on order information sent from the RIS 26 or the HIS 28 to the console 22. The order information is prepared by the doctor in the RIS 26 or the HIS 28. The order information may include subject information for identifying the subject 14 (such as the name, age, and sex of the subject 14), and may further include information of the radiation output apparatus 18 and the electronic cassette 20 to be used in the image capturing process, the imaging area of the subject 14, the procedure of the image capturing process, etc. The image capturing conditions may include various conditions for emitting the radiation 16 to the imaging area of the subject 14 (such as the tube voltage and tube current of the radiation source 30 and the exposure time with the radiation 16).

In step S2, the doctor grips the handle 54 of the electronic cassette 20 stored in a certain storage and transports the electronic cassette 20 onto the image capturing base 12. In step S3, the doctor lays the subject 14 on the image capturing base 12 and the electronic cassette 20 to locate the imaging area of the subject 14 in the image capturable area 52. Thus, the positioning of the imaging area is carried out on the image capturable area 52.

In this case, the power supply device 116 continuously supplies electric power to the cassette control device 110, the communication device 114, the acceleration sensor 56, and the pressure sensor 58. Therefore, the acceleration sensor 56 successively detects the acceleration of the electronic cassette 20 and successively sends the detection signals indicating the detected acceleration values to the cassette control device 110. The pressure sensor 58 successively detects the external pressure applied to the electronic cassette 20 and successively sends the detection signals indicating the detected pressure values to the cassette control device 110.

When the imaging area of the subject 14 is positioned in the image capturable area 52, a pressure is applied by the subject 14 to the electronic cassette 20. The pressure sensor 58 detects the pressure applied by the subject 14, and sends the detection signal indicating the pressure to the cassette control device 110. In a case where the pressure value of the detection signal is at a level appropriate for the subject 14 on the electronic cassette 20, the shock prediction judgment part 182 judges that the electronic cassette 20 is in the process of positioning the subject 14.

Based on the judgment by the shock prediction judgment part 182, the cassette control device 110 acts to start the electric power supply from the power supply device 116 to the drive circuit device 68, the display operation device 122, and the speaker 124. Thus, the bias supply 162 starts to supply the bias voltage to the pixels 160, so that the pixels 160 become capable of storing the electric charges. Furthermore, the display operation device 122 displays various information and become capable of the input operation by the doctor, and the speaker 124 becomes capable of outputting sounds corresponding to signals from the cassette control device 110 to the outside. Consequently, the electronic cassette 20 is converted from the sleep state to the active state.

Based on the judgment by the shock prediction judgment part 182, the cassette control device 110 further acts to send, to the console 22 via the wireless communication through the communication device 114, a request signal for requesting to send the order information and the image capturing conditions. The console 22 receives the request signal, then sends the order information and the image capturing conditions to the electronic cassette 20 via the wireless communication, and sends the image capturing conditions to the radiation output apparatus 18 via the wireless communication. Consequently, in the radiation output apparatus 18, the received image capturing conditions are registered in the radiation control unit 32. Furthermore, in the electronic cassette 20, the received order information and image capturing conditions are registered in the cassette control device 110. When the cassette control device 110 receives the order information and the image capturing conditions, the cassette control device 110 may act to display them on the display operation device 122.

In step S4, when the radiation switch 34 is pressed halfway by the doctor, the radiation control unit 32 makes a preparation to emit the radiation 16 and sends the signal indicating the emission preparation to the console 22 via the wireless communication. The console 22 sends, to the electronic cassette 20 via the wireless communication, a synchronization control signal for synchronizing with the emission of the radiation 16 from the radiation source 30. In the electronic cassette 20, the cassette control device 110 receives the synchronization control signal, and then may act to display information indicating the start of the emission preparation on the display operation device 122 and to output a sound corresponding to the information from the speaker 124 to the outside.

Based on the synchronization control signal, the contact instruction part 186 sends, to the inflator 120, the operation start instruction signal for driving the air-bag 240. When the operation start instruction signal is entered, the inflator 120 ignites the ignition agent to generate the inert gas and supplies the inert gas to the air-bag 240. The air-bag 240 is inflated toward the radiation conversion panel 64 by the inert gas supplied from the inflator 120, whereby the scintillator panel 62 is shifted toward the radiation conversion panel 64, the second surface of the buffer layer 280 is brought into contact with the radiation conversion panel 64 as shown in FIG. 4B, and the electronic cassette 20 becomes capable of detecting the radiation 16 (step S5).

In a case where the second surface of the buffer layer 280 is brought into contact with the radiation conversion panel 64, the cassette control device 110 may act to display information indicating the contact on the display operation device 122 and to output a sound corresponding to the information from the speaker 124 to the outside. Consequently, the doctor can easily recognize that the electronic cassette 20 becomes capable of detecting the radiation 16.

When the radiation switch 34 is completely pressed by the doctor in step S6, the radiation control unit 32 acts to emit the radiation 16 from the radiation source 30 to the imaging area of the subject 14 for a predetermined time included in the image capturing conditions (step S7). In this step, at the start of the emission of the radiation 16, the radiation control unit 32 may send, to the console 22 via the wireless communication, the signal indicating the start of the emission of the radiation 16. The console 22 transfers the sent signal to the electronic cassette 20. When the electronic cassette 20 receives the signal, the cassette control device 110 may act to display information indicating the emission on the display operation device 122 and to output a sound corresponding to the information from the speaker 124 to the outside.

In step S8, the radiation 16 is transmitted through the imaging area of the subject 14 and reaches the radiation detector 66 in the electronic cassette 20. In a case where the radiation detector 66 is of the ISS type shown in FIG. 4B, the radiation 16 is introduced through the radiation conversion panel 64 and the buffer layer 280 into the columnar crystal structure 148 in the scintillator 150.

The columnar crystal structure 148 emits the visible light (the fluorescent light) with an intensity corresponding to the radiation 16, and the fluorescent light is introduced from the columns in the columnar crystal structure 148 through the buffer layer 280 to the radiation conversion panel 64. Though part of the fluorescent light may be transmitted toward the non-columnar crystal portion 146, the part can be reflected by the reflective film 260 (or the support board 144) and the non-columnar crystal portion 146 toward the buffer layer 280 and may be introduced into the radiation conversion panel 64.

The pixels 160 in the radiation conversion panel 64 converts the fluorescent light into the electric signals, and stores the electric signals as electric charges. Then, the electric charges corresponding to the radiographic image of the imaging area of the subject 14, stored in the pixels 160, are read out based on a drive signal sent from the readout control part 180 in the cassette control device 110 to the gate drive part 168.

The gate drive part 168 selects the gate lines 164 in 0th to final rows sequentially, and outputs gate signals to the selected gate lines 164 sequentially. Then, the TFTs 72 are turned on by the gate signals sequentially, and the electric charges stored in the pixels 160 in the 0th to final rows are read out sequentially row by row. The electric charges, which are read out from the pixels 160 sequentially row by row, are sent through the signal lines 166 to the charge amplifiers 170 column by column, transferred through the multiplexer part 172 and the AD conversion part 174, and stored as the digital electric signals in the memory 112 (step S9). Thus, one-row image data are stored in the memory 112 sequentially row by row.

In this step, the cassette control device 110 acts to perform the image correction processing for correcting the digital pixel signal values in accordance with the shape of the distal end portion of the columnar crystal structure 148. In a case where the distal end portion of the columnar crystal structure 148 is convexly curved as shown in FIGS. 4B, 5B, 7B, and 8B or tapered as shown in FIG. 6B toward the radiation conversion panel 64, the top shape may cause image distortion. Therefore, the digital pixel signal values are corrected depending on the distortion. Thus, the image data obtained by the image correction processing are stored in the memory 112 sequentially row by row.

The radiographic image, stored in the memory 112 after the image correction processing, is sent in combination with cassette ID information for identifying the electronic cassette 20 through the communication device 114 to the console 22 via the wireless communication. The console 22 acts to display the sent radiographic image and cassette ID information on the display device 24 (step S10). The cassette control device 110 may act to display the radiographic image and the cassette ID information on the display operation device 122.

The doctor visually recognizes the information on the display device 24 or the display operation device 122 and understands that the radiographic image is recorded. Then, the doctor operates the display operation device 122 to instruct to separate the buffer layer 280 from the radiation conversion panel 64. The separation instruction part 184 sends the operation stop instruction signal to the inflator 120 based on the instruction by the doctor. The inflator 120 stops the inert gas supply to the air-bag 240 based on the operation stop instruction signal. Consequently, the inert gas in the air-bag 240 is discharged from the discharge hole (not shown) and the air-bag 240 is deflated, so that the buffer layer 280 (the scintillator panel 62) is separated from the radiation conversion panel 64 (step S11).

The cassette control device 110 may act to display information indicating the separation of the buffer layer 280 from the radiation conversion panel 64 on the display operation device 122 and to output a sound corresponding to the information from the speaker 124 to the outside. Consequently, the doctor judges that the electronic cassette 20 can be transported without incident, and releases the subject 14 from the positioned state (step S12). Also in this step, the pressure sensor 58 successively detects the external pressure applied to the electronic cassette 20 and successively sends the detection signals to the cassette control device 110. When the pressure of the detection signal is lowered from the pressure of the subject 14 in the positioned state to approximately zero, the shock prediction judgment part 182 judges that the subject 14 is released from the positioned state.

Based on the judgment by the shock prediction judgment part 182, the cassette control device 110 acts to stop the electric power supply from the power supply device 116 to the drive circuit device 68, the display operation device 122, and the speaker 124. Thus, the bias voltage supply from the bias supply 162 to the pixels 160 is stopped, and also the display operation device 122 and the speaker 124 are stopped. Consequently, the electronic cassette 20 is converted from the active state into the sleep state.

In step S13, the doctor confirms that the image on the display operation device 122 is cleared and the electronic cassette 20 is converted into the sleep state. Then, the doctor grips the handle 54 of the electronic cassette 20, and transports the electronic cassette 20 to the certain storage.

In FIG. 11, the buffer layer 280 and the radiation conversion panel 64 are brought into contact with each other in step S5 and are separated from each other in step S11. This embodiment is not limited to FIG. 11 as long as the buffer layer 280 and the radiation conversion panel 64 are in (tight) contact with each other at least during the emission of the radiation 16. Alternatively, for example, the buffer layer 280 and the radiation conversion panel 64 may be brought into contact with each other in a case where the entire electronic cassette 20 is converted from the sleep state into the active state in step S3, and the buffer layer 280 and the radiation conversion panel 64 may be separated from each other in a case where the entire electronic cassette 20 is converted from the active state into the sleep state in step S12.

The operation of FIG. 12 will be described below.

The acceleration sensor 56 successively detects the acceleration of the electronic cassette 20 and successively sends the detection signals indicating the detected acceleration values to the cassette control device 110, while the pressure sensor 58 successively detects the external pressure applied to the electronic cassette 20 and successively sends the detection signals indicating the detected pressure values to the cassette control device 110 (step S21).

In this case, whenever the detection signals are sent from the acceleration sensor 56 and the pressure sensor 58 into the cassette control device 110, the shock prediction judgment part 182 judges whether or not the acceleration value corresponding to the detection signal from the acceleration sensor 56 is larger than the predetermined threshold value and whether or not the pressure value corresponding to the detection signal from the pressure sensor 58 is larger than the predetermined threshold value (acceptable value) (step S22).

In a case where the value of the detected acceleration and the value of the detected pressure do not reach the predetermined threshold values in step S22 (step S22: NO), the shock prediction judgment part 182 judges that the electronic cassette 20 is not subjected to a large shock causing the breakage (fracture) or cracking of the columnar crystal structure 148 or the surface scratch of the radiation conversion panel 64, and is kept in the waiting state until the next detection signal is entered.

On the other hand, when the detected acceleration or pressure value is larger than the predetermined threshold value in step S22 (step S22: YES), the shock prediction judgment part 182 judges that the breakage (fracture) or cracking of the columnar crystal structure 148 or the surface scratch of the radiation conversion panel 64 may be caused by the external shock (step S23), and sends the communication signal, which indicates that the external shock will be applied to the electronic cassette 20, to the separation instruction part 184.

In step S24, the separation instruction part 184 sends the operation stop instruction signal to the inflator 120 based on the communication signal from the shock prediction judgment part 182, and the inflator 120 stops the inert gas supply to the air-bag 240 based on the sent operation stop instruction signal. Then, the air-bag 240 discharges the inert gas from the discharge hole to be shrunk toward the bottom plate 140. Consequently, the buffer layer 280 and the scintillator 150 are separated from the radiation conversion panel 64 as shown in FIG. 4A.

Furthermore, when the communication signal is entered from the shock prediction judgment part 182, the separation instruction part 184 sends, to the display operation device 122 and the speaker 124, a warning signal indicating that the air-bag 240 will be deflated due to the external shock and that the buffer layer 280 and the scintillator 150 will be separated from the radiation conversion panel 64. The display operation device 122 displays the information of the warning signal, and the speaker 124 outputs a sound corresponding to the warning signal to the outside (step S25). The doctor can visually recognize the information on the display operation device 122 or hear the sound from the speaker 124 or both to understand that the air-bag 240 will be deflated due to the external shock and that the buffer layer 280 and the scintillator 150 will be separated from the radiation conversion panel 64.

In this manner, the air-bag 240 is deflated, and the buffer layer 280 and the scintillator 150 are separated from the radiation conversion panel 64. Therefore, even if practically the electronic cassette 20 is dropped onto the floor or the subject 14 violently contacts with the exposed surface 44, whereby the electronic cassette 20 is subjected to the external shock causing the breakage (fracture) or cracking of the columnar crystal structure 148 or the surface scratch of the radiation conversion panel 64 (step S26), the columnar crystal structure 148 can be appropriately protected.

Then, in a case where a predetermined time has elapsed from the deflation of the air-bag 240 (step S27: YES), the shock prediction judgment part 182 judges that the external shock is no longer likely to be applied to the electronic cassette 20, and sends the communication signal to the contact instruction part 186. In step S28, the contact instruction part 186 sends the operation start instruction signal to the inflator 120 based on the communication signal, and the inflator 120 restarts to supply the inert gas to the air-bag 240 based on the sent operation start instruction signal. Consequently, the air-bag 240 is inflated by the supplied inert gas, the buffer layer 280 and the scintillator 150 are brought into contact with the radiation conversion panel 64 again, and thus the electronic cassette 20 is returned (restored) to the original state.

Furthermore, the contact instruction part 186 acts to clear the warning on the display operation device 122 and to stop the warning sound from the speaker 124 based on the communication signal (step S29). Consequently, the doctor can easily recognize that the buffer layer 280 and the scintillator 150 are brought into contact with the radiation conversion panel 64 again, and thus the electronic cassette 20 is returned to the original state.

Even during the deflation of the air-bag 240, the acceleration sensor 56 can successively detect the acceleration of the electronic cassette 20 and can successively send the detection signals indicating the detected acceleration values to the cassette control device 110, while the pressure sensor 58 can successively detect the external pressure applied to the electronic cassette 20 and can successively send the detection signals indicating the detected pressure values to the cassette control device 110. Therefore, when the acceleration and pressure values become smaller than the predetermined threshold values after the deflation of the air-bag 240, the shock prediction judgment part 182 can judge that the external shock is no longer likely to be applied to the electronic cassette 20, and can send the communication signal to the contact instruction part 186. Also in this case, the radiation conversion panel 64 and the scintillator 150 can be reliably returned to the original state.

The image on the display operation device 122 and the sound from the speaker 124 are used to give the warning in the above description. Alternatively, the separation instruction part 184 may send the warning signal through the communication device 114 to the console 22 via the wireless communication. In this case, the console 22 acts to display a warning corresponding to the warning signal on the display device 24. The doctor can visually recognize the warning information on the display device 24 to understand that the air-bag 240 is deflated due to the external shock and that the buffer layer 280 and the scintillator 150 are separated from the radiation conversion panel 64. Furthermore, the contact instruction part 186 may send a signal for clearing the displayed warning through the communication device 114 to the console 22 via the wireless communication. In this case, the console 22 acts to clear the warning on the display device 24 based on the sent signal. Consequently, the doctor can recognize that the buffer layer 280 and the scintillator 150 are brought into contact with the radiation conversion panel 64 again, and thus the electronic cassette 20 is returned to the original state.

[Advantageous Effects of the Embodiment]

As described above, in the electronic cassette 20 according to this embodiment, the distal end portion of the columnar crystal structure 148 is convexly curved and protruded toward the radiation conversion panel 64, the first surface of the buffer layer 280 permeable to the visible light can be bonded to the curved distal end portion with the protective moisture-proof material 152 and the adhesive layer 282 interposed therebetween, and the second surface (opposite to the first surface) of the buffer layer 280 can be brought into contact with the radiation conversion panel 64. Therefore, the top of the columnar crystal structure 148, bonded to the first surface of the buffer layer 280, can be brought into (tight) contact with the radiation conversion panel 64 via the second surface.

The electronic cassette 20 contains the scintillator 150 having the columnar crystal structure 148, the buffer layer 280, and the radiation conversion panel 64. Even in a case where the scintillator 150 and the buffer layer 280 are frequently brought into contact with and separated from the radiation conversion panel 64 depending on the state of the electronic cassette 20, the columnar crystal structure 148 can be prevented from being broken (fractured) or cracked in the process of pressing the scintillator 150 against the radiation conversion panel 64.

The buffer layer 280 is disposed on the distal end portion of the columnar crystal structure 148, and the columnar crystal structure 148 is pressed onto the radiation conversion panel 64 with the buffer layer 280 interposed therebetween. Therefore, the columnar crystal structure 148 can be reliably prevented from being broken (fractured) or cracked. In addition, even if the distal end portion of the columnar crystal structure 148 (the protective moisture-proof material 152) is slightly uneven, the second surface of the buffer layer 280 can be a curved or flat surface without the unevenness. Consequently, if the buffer layer 280 is brought into contact with the radiation conversion panel 64, the surface of the radiation conversion panel 64 is not scratched.

In this embodiment, the distal end portion of the columnar crystal structure 148 is convexly curved and protruded toward the radiation conversion panel 64, and the first surface of the buffer layer 280 is bonded to and curved along the convexly curved distal end portion of the columnar crystal structure 148 (see FIGS. 4A to 5B and 7A to 8B). Alternatively, the distal end portion of the columnar crystal structure 148 in the protective moisture-proof material 152 is tapered toward the radiation conversion panel 64, the center of the distal end portion is approximately parallel to the radiation conversion panel 64, and the buffer layer 280 is bonded to the center of the distal end portion (see FIGS. 6A and 6B). Consequently, the contact between the buffer layer 280 and the radiation conversion panel 64 can be improved in the process of pressing the buffer layer 280 onto the radiation conversion panel 64.

In the cassette control device 110, the digital pixel signal values (the radiographic image) read from the radiation conversion panel 64 are corrected depending on the shape of the distal end portion of the columnar crystal structure 148. Therefore, the radiographic image can be appropriately acquired regardless of the shape of the distal end portion.

In this embodiment, the scintillator 150 (the columnar crystal structure 148 formed therein) and the radiation conversion panel 64 are brought into contact with each other without using the adhesive agent. Therefore, the problem of the light detection deterioration, caused by the adhesive agent deteriorated under the radiation 16, can be prevented. Consequently, the ISS type radiation detector 66 can exhibit an improved light detection function.

In a case where the buffer layer 280 is the flexible transparent plastic sheet permeable to the fluorescent light (such as the silicone rubber film, the polyimide film, the polyarylate film, the biaxially-oriented polystyrene film, or the aramid film) and has a thickness of less than 50 μm (more preferably less than 30 μm), the buffer layer 280 is substantially not warped or is only slightly warped due to the temperature change of the electronic cassette 20. Thus, in a case where the buffer layer 280 is the thin, flexible, light transmittable, plastic sheet, the columnar crystal structure 148 can be prevented from being broken and cracked in the process of pressing the buffer layer 280 onto the radiation conversion panel 64. Furthermore, since the distance between the scintillator 150 and the radiation conversion panel 64 is not large, the resultant radiographic image is not blurred.

The surface of the radiation conversion panel 64, which is brought into contact with the second surface of the buffer layer 280, is planarized by using the tetrafluoroethylene resin film. Therefore, when the buffer layer 280 is pressed against the radiation conversion panel 64, the second surface of the buffer layer 280 can be brought into tight contact with the surface of the radiation conversion panel 64, whereby the fluorescent light can be efficiently introduced from the scintillator 150 into the radiation conversion panel 64. In addition, the scratch or the like on the radiation conversion panel 64 can be prevented in the process of pressing the buffer layer 280 onto the radiation conversion panel 64.

The scintillator 150 having the columnar crystal structure 148 of the CsI is sealed by the protective moisture-proof material 152, and the reflective film 260 is disposed on the non-columnar crystal portion 146. Therefore, the scintillator 150 can be appropriately protected against moisture. Furthermore, the fluorescent light emitted toward the non-columnar crystal portion 146 is reflected by the reflective film 260 and the non-columnar crystal portion 146 toward the buffer layer 280. Therefore, the quantity of the fluorescent light introduced into the radiation conversion panel 64 can be increased.

The scintillator 150 may be vapor-deposited on the support board 144, and the scintillator 150 and the support board 144 may be used in the scintillator panel 62 without removing the support board 144. In this case, it is not necessary to separate the scintillator 150 from the support board 144. Therefore, the electronic cassette 20 can be efficiently produced.

The scintillator 150 is pressed against the radiation conversion panel 64 with the buffer layer 280 interposed therebetween as described above. Therefore, even if the thickness of the scintillator 150 varies with the position, the buffer layer 280 and the radiation conversion panel 64 can be appropriately brought into tight contact with each other. In addition, the scintillator 150 is not vapor-deposited on the radiation conversion panel 64. Therefore, in a case where the scintillator 150 is unsuccessfully vapor-deposited on the support board 144, the radiation conversion panel 64 can be reused.

The scintillator 150 and the radiation conversion panel 64 are independent from each other. Therefore, in a case where one of the components is broken or crashed, the other component can be reused. Thus, the electronic cassette 20 is excellent in reworkability.

In a case where the buffer layer 280 and the radiation conversion panel 64 are repeatedly contacted and separated, the buffer layer 280 may be damaged. Therefore, the buffer layer 280 is preferably a replaceable member.

In this embodiment, the distal end portion of the columnar crystal structure 148 has the convexly curved shape. The support board 144 may be convexly curved toward the radiation conversion panel 64. In this case, the distal end portion of the columnar crystal structure 148 can be protruded along the shape of the support board 144 by forming the scintillator 150 with a uniform thickness.

This embodiment achieves a further effect as follows. At least while the radiation 16 is emitted to the radiation detector 66, the scintillator 150 and the radiation conversion panel 64 are brought into contact with each other with the buffer layer 280 interposed therebetween. When the acceleration value detected by the acceleration sensor 56, the pressure value detected by the pressure sensor 58, or the drop time of the electronic cassette 20 based on the acceleration becomes larger than the predetermined threshold value, the buffer layer 280 and the scintillator 150 are separated from the radiation conversion panel 64 (the contact control of the scintillator 150 with the radiation conversion panel 64 is stopped). Therefore, in a case where the electronic cassette 20 is subjected to the external shock, the scintillator 150 (the columnar crystal structure 148 therein) can be appropriately protected against the shock, and the columnar crystal structure 148 can be reliably prevented from being broken (fractured) or cracked by the shock. Furthermore, even in a case where the columnar crystal structure 148 is displaced by the shock, the surface of the radiation conversion panel 64 can be reliably prevented from being scratched due to the displacement. In addition, in a case where the electronic cassette 20 is likely to be subjected to the external shock, the columnar crystal structure 148 can be reliably protected against the shock. Therefore, the electronic cassette 20 can maintain excellent image capturing performance regardless of the shock.

When the inert gas supply from the inflator 120 to the air-bag 240 is stopped and the inert gas in the air-bag 240 is discharged, the air-bag 240 is shrunk in the thicknesswise direction of the casing 40, whereby the buffer layer 280 and the scintillator 150 are separated from the radiation conversion panel 64. Therefore, the buffer layer 280 and the scintillator 150 can be rapidly separated from the radiation conversion panel 64 in preparation for the external shock. The buffer layer 280 and the scintillator 150 can be brought again into contact with the radiation conversion panel 64 by restarting the inert gas supply from the inflator 120 to inflate the air-bag 240. Therefore, the buffer layer 280 and the scintillator 150 can be temporarily separated from the radiation conversion panel 64, and can be readily returned (restored) to the original state.

As described above, when the radiation switch 34 is pressed halfway by the doctor, the radiation control unit 32 sends the signal indicating the preparation for the emission of the radiation 16 to the console 22 via the wireless communication, and the console 22 sends the synchronization control signal to the electronic cassette 20 via the wireless communication.

In this embodiment, the inflator 120 and the air-bag 240 may be stopped to separate the scintillator 150 and the buffer layer 280 from the radiation conversion panel 64 in time periods the electronic cassette 20 is likely to be subjected to the external shock before the preparation for the emission of the radiation 16 and after the completion of the emission of the radiation 16. Meanwhile, the inflator 120 and the air-bag 240 may be driven to bring the buffer layer 280 and the scintillator 150 into contact with the radiation conversion panel 64 after the electronic cassette 20 receives the synchronization control signal until the emission of the radiation 16 is completed. For example, in the step of positioning the subject 14, the excessive load (pressure) may be applied by the subject 14 to the electronic cassette 20, so that the columnar crystal structure 148 may be broken or cracked, and the surface of the radiation conversion panel 64 may be scratched. Therefore, the scintillator 150 and the buffer layer 280 are separated from the radiation conversion panel 64 while the electronic cassette 20 is likely to be subjected to such a shock.

The electronic cassette 20 is less likely to be subjected to the external shock during the emission of the radiation 16, and the buffer layer 280 and the scintillator 150 are brought into contact with the radiation conversion panel 64 only during the emission of the radiation 16 in this embodiment. Therefore, the scintillator 150 can be appropriately protected against the shock, the electronic cassette 20 can be prevented from being deteriorated in the image capturing performance, and the radiographic image can be appropriately acquired. Thus, in the electronic cassette 20, based on the registered order information, the scintillator 150 and the buffer layer 280 can be brought into contact with the radiation conversion panel 64 before the emission of the radiation 16 to the subject 14, and the scintillator 150 and the buffer layer 280 can be separated from the radiation conversion panel 64 after the emission of the radiation 16.

[Modifications of the Embodiment]

First to fourth modifications of this embodiment will be described below with reference to FIGS. 13A to 16B.

Components of the modifications, which are identical to those of FIGS. 1 to 12, are denoted by identical reference numbers, and detailed explanations thereof are omitted.

Figure 13A:
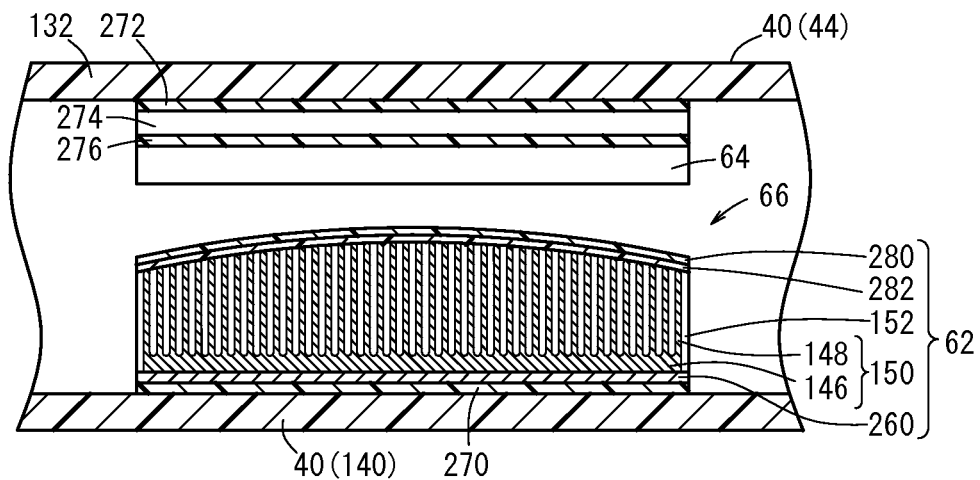
FIGS. 13A and 13B are cross-sectional views of a principal part according to a first modification of the embodiment.
Figure 13B:
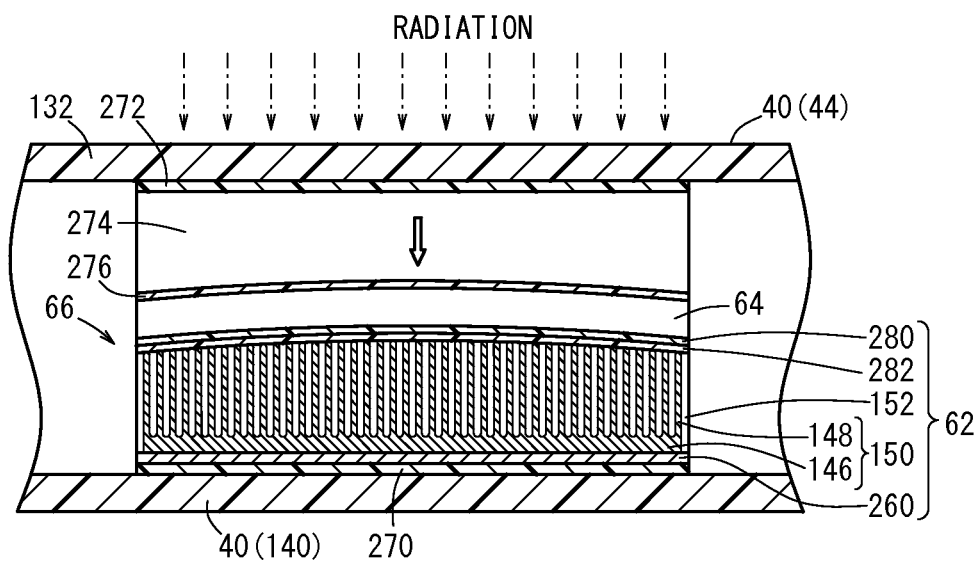

In the first modification, as shown in FIGS. 13A and 13B, an air-bag 274 (contact mechanism) is interposed between the top plate 132 and the radiation conversion panel 64.

In this case, the air-bag 274 is bonded to the top plate 132 by an adhesive layer 272, and the radiation conversion panel 64 is bonded to the air-bag 274 by an adhesive layer 276. The reflective film 260 is bonded to the bottom plate 140 by an adhesive layer 270.

When the air-bag 274 is inflated in the thicknesswise direction of the casing 40 by the inert gas from the inflator 120 as shown in FIG. 13B, the buffer layer 280 and the radiation conversion panel 64 are brought into contact with each other and become capable of capturing the radiographic image.

When the shock prediction judgment part 182 judges that the electronic cassette 20 will be subjected to the external shock, the separation instruction part 184 acts to stop the inert gas supply from the inflator 120 based on the communication signal from the shock prediction judgment part 182. Then, the inert gas in the air-bag 274 is discharged from a discharge hole (not shown), whereby the air-bag 274 is shrunk in the thicknesswise direction of the casing 40 (toward the top plate 132). Consequently, the buffer layer 280 and the radiation conversion panel 64 can be separated from each other as shown in FIG. 13A.

In a case where the electronic cassette 20 is not likely to be subjected to the external shock, the contact instruction part 186 acts to activate the inflator 120 again. Then, the inert gas supply to the air-bag 274 is restarted, whereby the radiation conversion panel 64 is brought into contact with the buffer layer 280 and the scintillator 150 again as shown in FIG. 13B.

Thus, also in the first modification, the radiation conversion panel 64 can be contacted with and separated from the buffer layer 280 and the scintillator 150 (the contact control of the radiation conversion panel 64 with the buffer layer 280 and the scintillator 150 can be executed and stopped) by using the air-bag 274 and the inflator 120. Consequently, the first modification can achieve the same effects as the above embodiment.

Figure 14A:
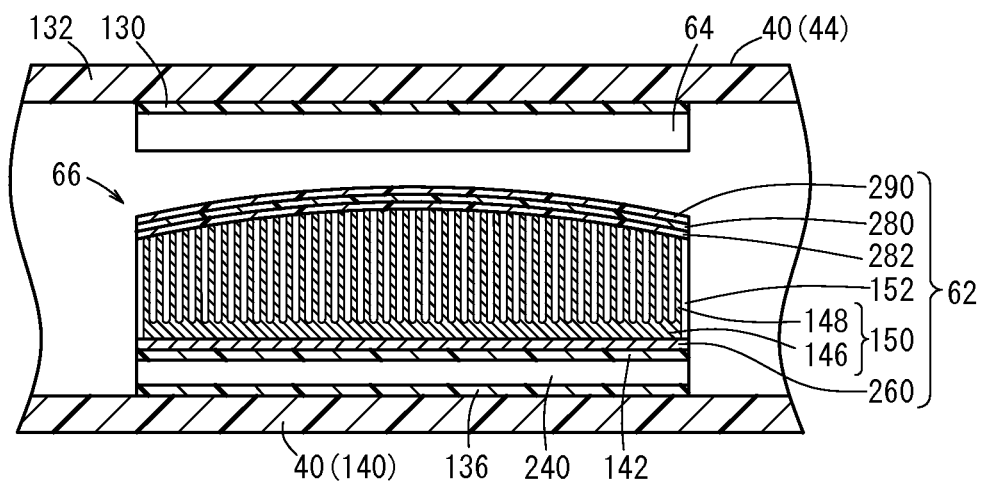
FIGS. 14A and 14B are cross-sectional views of a principal part according to a second modification of the embodiment.
Figure 14B:
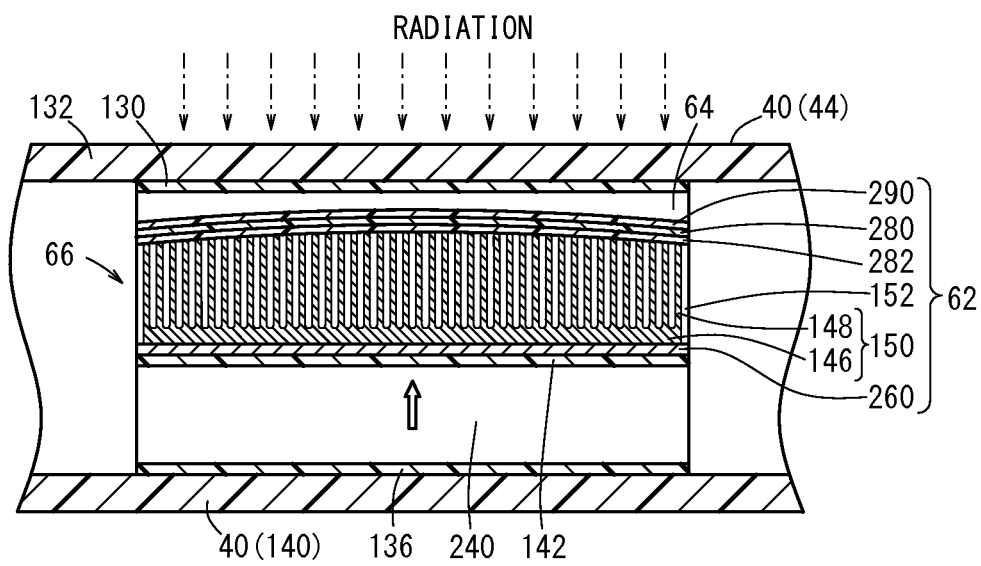

In the second modification, as shown in FIGS. 14A and 14B, the second surface of the buffer layer 280 is coated with a weak adhesive layer 290. In this case, a sticking or adhesive agent in the adhesive layer 282 has a sticking or adhesive power larger than at least that of the weak adhesive layer 290. Therefore, in a case where the buffer layer 280 and the radiation conversion panel 64 are brought into contact with each other with the weak adhesive layer 290 interposed therebetween as shown in FIG. 14B, the tight contact between the buffer layer 280 and the radiation conversion panel 64 can be further improved. Furthermore, the buffer layer 280 and the radiation conversion panel 64 can be easily separated from each other due to the weak adhesive layer 290 as shown in FIG. 14A. Also the second modification can achieve the same effects as the above embodiment.

Figure 15A:
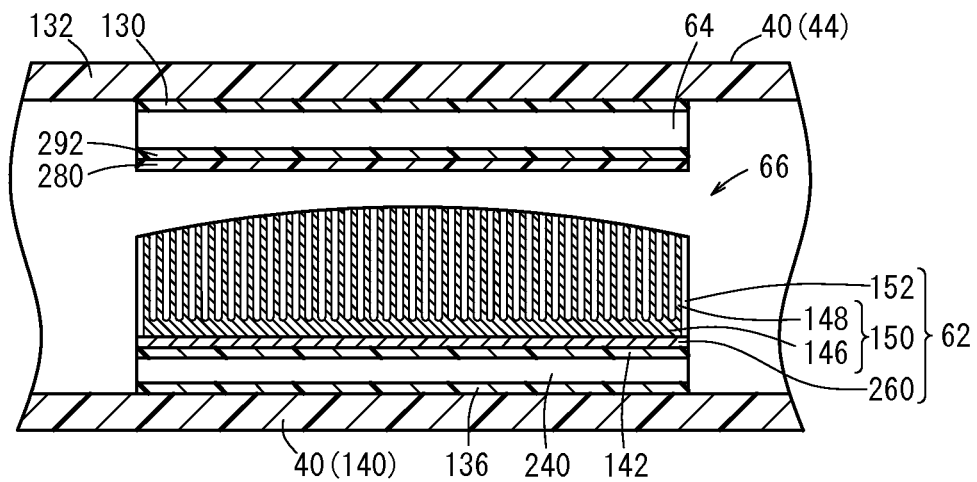
FIGS. 15A and 15B are cross-sectional views of a principal part according to a third modification of the embodiment.
Figure 15B:
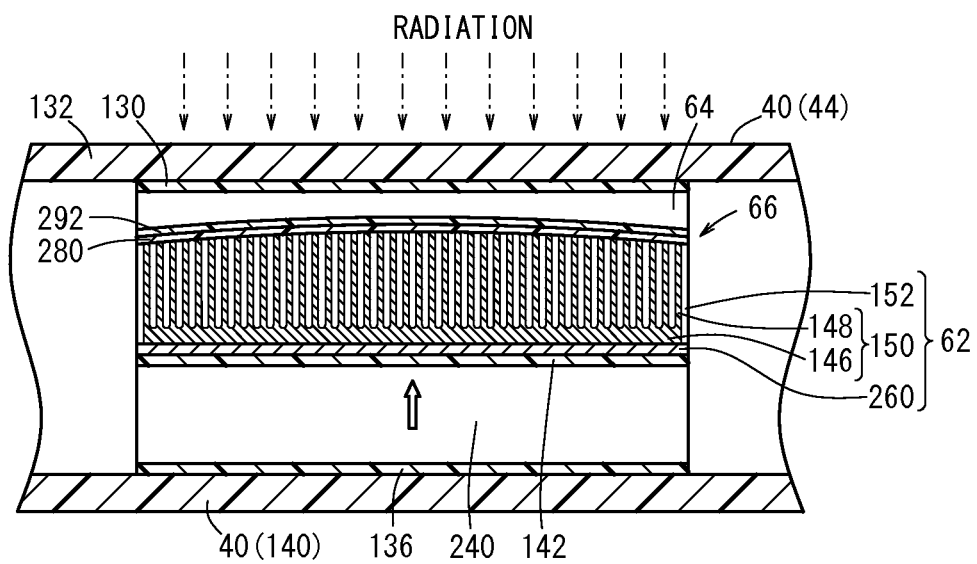

In the third modification, as shown in FIGS. 15A and 15B, the buffer layer 280 is bonded to the radiation conversion panel 64 by an adhesive layer 292. Therefore, the distal end portion of the columnar crystal structure 148 in the scintillator panel 62 does not have the buffer layer 280. In a case where the distal end portion of the columnar crystal structure 148 is pressed onto the radiation conversion panel 64 as shown in FIG. 15B, regardless of the unevenness of the distal end portion of the columnar crystal structure 148, the buffer layer 280 can prevent the penetration of the distal end portion into the protective moisture-proof material 152. Also the third modification can achieve the same effects as the above embodiment.

Figure 16A:
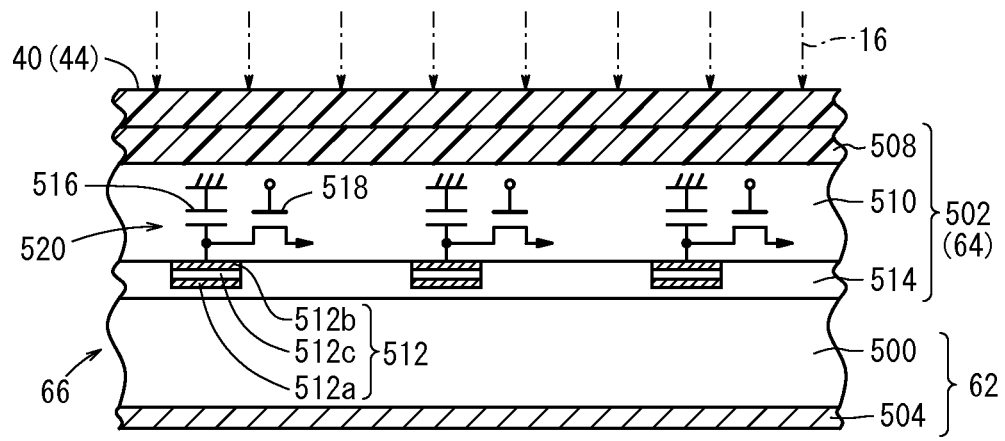
FIG. 16A is a schematic explanatory view of an inner structure of a cassette according to a fourth modification of the embodiment.
Figure 16B:
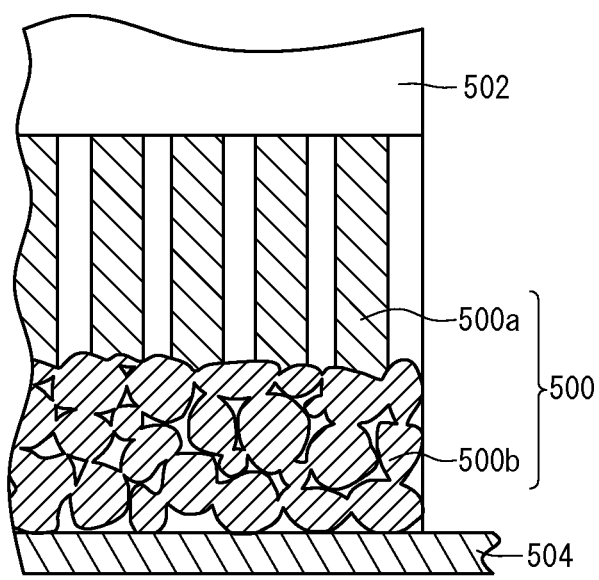
FIG. 16B is a schematic explanatory view of an example of a scintillator shown in FIG. 16A.

The radiation detector 66 may have a structure shown in FIGS. 16A and 16B (the fourth modification). In the fourth modification, a specific structure of the radiation detector 66, which contains the CsI scintillator used in the above embodiment, will be described in detail below.

In the fourth modification, as shown in FIGS. 16A and 16B, the radiation detector 66 has a scintillator 500 for converting the radiation 16 transmitted through the subject 14 into the visible light (absorbing the radiation 16 and emitting the visible light), and further has a radiation detection part 502 for converting the visible light from the scintillator 500 into the electric signals (the electric charges) corresponding to the radiographic image. The scintillator 500 corresponds to the above scintillator 150, and the radiation detection part 502 corresponds to the radiation conversion panel 64. The protective moisture-proof material 152 is omitted in FIGS. 16A and 16B.

As described above, the radiation detector 66 may be the ISS type radiation detector (wherein the radiation detection part 502 and the scintillator 500 are arranged in this order from the exposed surface 44 to be irradiated with the radiation 16 as shown in FIGS. 16A and 16B) or the PSS type radiation detector (wherein the scintillator 500 and the radiation detection part 502 are arranged in this order from the exposed surface 44).

The scintillator 500 emits the light more intensely at the side closer to the exposed surface 44, which is irradiated with the radiation 16. In the ISS type radiation detector 66, the light emitting portion of the scintillator 500 is closer to the radiation detection part 502. Therefore, as compared with the PSS type radiation detector 66, the ISS type radiation detector 66 exhibits a higher resolution of the radiographic image in the image capturing process and a larger visible light quantity received in the radiation detection part 502. Thus, the ISS type radiation detector 66 exhibits a sensitivity higher than that of the PSS type radiation detector 66 (in the electronic cassette 20).

The scintillator 500 may be composed of a material such as CsI:Tl, CsI:Na (sodium-activated cesium iodide), GOS ($Gd_2O_2S$:Tb), or the like.

An example of the scintillator 500 having a columnar crystal region, which is produced by vapor-depositing a material containing CsI on an evaporation board 504 corresponding to the above support board 144, is shown in FIG. 16B. Thus, the scintillator panel 62 contains the evaporation board 504 and the scintillator 500 (see FIG. 16A).

More specifically, in the scintillator 500 shown in FIG. 16B, the columnar crystal region containing columnar crystals 500a is formed closer to the exposed surface 44 to be irradiated with the radiation 16 (the radiation detection part 502), and a non-columnar crystal region containing non-columnar crystals 500b is formed remotely from the exposed surface 44. The columnar crystals 500a correspond to the columnar crystal structure 148 (see FIGS. 4A, 4B, 6A to 8B, and 13A to 15B), and the non-columnar crystals 500b correspond to the non-columnar crystal portion 146. The evaporation board 504 is preferably composed of a highly heat-resistant material such as low-cost aluminum (Al). The columnar crystals 500a in the scintillator 500 have a substantially uniform average diameter along the longitudinal direction of the columnar crystals 500a.

As described above, the scintillator 500 includes the columnar crystal region (the columnar crystals 500a) and the non-columnar crystal region (the non-columnar crystals 500b). The columnar crystal region of the columnar crystals 500a, which are capable of highly efficient light emission, is disposed in close proximity to the radiation detection part 502. Therefore, the visible light generated in the scintillator 500 travels through the columnar crystals 500a to the radiation detection part 502. As a result, the diffusion of the visible light emitted toward the radiation detection part 502 can be prevented, so that the radiographic image detected by the electronic cassette 20 can be prevented from blurring. In addition, the visible light that reaches the deep region (the non-columnar crystal region) of the scintillator 500 is reflected by the non-columnar crystals 500b toward the radiation detection part 502. Therefore, the amount of the visible light introduced into the radiation detection part 502 (the efficiency of detecting the visible light from the scintillator 500) can be improved.

In this embodiment, the top of the columnar crystal structure 148 corresponding to the columnar crystals 500a may be convexly curved at the center, and the thickness of the scintillator 150 corresponding to the scintillator 500 may vary with the position (see FIGS. 4A to 5B, 7A to 8B, and 13A to 15B). In the scintillator 500, in a case where the columnar crystal region closer to the exposed surface 44 has a thickness t1 and the non-columnar crystal region closer to the evaporation board 504 has a thickness t2, the thicknesses t1 and t2 preferably satisfy the relationship $0.01 \leq (t2/t1) \leq 0.25$ at least around the center of the scintillator 500.

In a case where the thickness t1 of the columnar crystal region and the thickness t2 of the non-columnar crystal region satisfy the above relationship, the ratio in the thicknesswise direction of the scintillator 500 between the columnar crystal region having a high light emission efficiency and a visible light diffusion preventing capability and the non-columnar crystal region capable of reflecting the visible light can be within an appropriate range, to improve the light emission efficiency of the scintillator 500, the efficiency of detecting the visible light emitted from the scintillator 500, and the resolution of the radiographic image.

In a case where the thickness t2 of the non-columnar crystal region is too large, the region with the low light emission efficiency is increased to lower the sensitivity of the electronic cassette 20. Therefore, the ratio (t2/t1) is more preferably within a range of 0.02 to 0.1.

In the above example, the columnar crystal region and the non-columnar crystal region are arranged adjacent to each other in the scintillator 500. Alternatively, for example, a light reflecting layer made of Al or the like may be used instead of the non-columnar crystal region, and the scintillator 500 may have only the columnar crystal region. The scintillator 500 may have a structure different from these examples.

The radiation detection part 502 serves to detect the visible light emitted from the light emitting side (the columnar crystals 500a) of the scintillator 500. In the side elevation of FIG. 16A, an insulative substrate 508, a TFT layer 510, and photoelectric transducers 512 are stacked in this order from the exposed surface 44 along the direction of incident radiation 16. The photoelectric transducers 512 are covered with a planarization layer 514 formed on the bottom surface of the TFT layer 510.

The radiation detection part 502 is a TFT active matrix board containing the insulative substrate 508 and thereon a plurality of pixels 520 arranged in a matrix as viewed in plan (hereinafter referred to as a TFT board). Each of the pixels 520 includes the photoelectric transducer 512 such as a photodiode (PD), a storage capacitor 516, and a TFT 518.

The TFTs 518 correspond to the aforementioned TFTs 72 (see FIG. 10), and the photoelectric transducers 512 and the storage capacitors 516 correspond to the pixels 160.

The photoelectric transducer 512 is formed by disposing a photoelectric conversion film 512c between a lower electrode 512a in close proximity to the scintillator 500 and an upper electrode 512b in close proximity to the TFT layer 510. The photoelectric conversion film 512c absorbs the visible light emitted from the scintillator 500 and generates the electric charge corresponding to the absorbed visible light.

The lower electrode 512a is preferably composed of an electrically conductive material transparent at least to the emission wavelength of the scintillator 500 to inject the visible light emitted from the scintillator 500 into the photoelectric conversion film 512c. Specifically, the lower electrode 512a preferably contains a transparent conducting oxide (TCO) having a high visible light transmittance and a small resistance value.

The lower electrode 512a may be a thin film of a metal such as Au. However, the thin metal film with a light transmittance of 90% or more tends to exhibit a high resistance, and thus the TCO is preferred. For example, the lower electrode 512a preferably contains ITO (Indium Tin Oxide), IZO (Indium Zinc Oxide), AZO (Aluminum-doped Zinc Oxide), FTO (Fluorine-doped Tin Oxide), $SnO_2$, $TiO_2$, $ZnO_2$, or the like. Among these oxides, the ITO is most preferable in view of processing simplicity, low resistance, and transparency. The lower electrode 512a may be in the form of a single film, which is shared by all of the pixels 520. Alternatively, the lower electrode 512a may be divided for each of the pixels 520.

The photoelectric conversion film 512c may be composed of a material capable of absorbing the visible light to generate the electric charge, and may contain for example an amorphous silicon (a-Si), an organic photoconductor (OPC), etc. The photoelectric conversion film 512c containing the amorphous silicon can absorb the visible light emitted from the scintillator 500 within a wide wavelength range. However, in the case of forming the photoelectric conversion film 512c containing the amorphous silicon, it is necessary to carry out a vapor deposition process. Therefore, in a case where the insulative substrate 508 is composed of a synthetic resin, the heat resistance of the insulative substrate 508 has to be taken into account.

On the other hand, the photoelectric conversion film 512c composed of a material containing the organic photoconductor can exhibit an absorption spectrum with high absorption mainly in the visible range. Therefore, the photoelectric conversion film 512c hardly absorbs electromagnetic waves other than the visible light from the scintillator 500. Thus, the photoelectric conversion film 512c can be prevented from absorbing the radiation 16 such as the X-ray or γ-ray, thereby preventing noise from being generated.

The photoelectric conversion film 512c composed of the organic photoconductor can be formed by depositing the organic photoconductor on a target using a liquid discharge head such as an ink-jet head. Therefore, the target is not required to be heat-resistant. In fourth modification, the photoelectric conversion film 512c is composed of the organic photoconductor for this reason.

The photoelectric conversion film 512c composed of the organic photoconductor hardly absorbs the radiation 16. Therefore, in the ISS type radiation detector 66 (wherein the radiation 16 is transmitted through the radiation detection part 502), attenuation of the radiation 16 in the radiation detection part 502 can be reduced, and deterioration in sensitivity of the radiation 16 can be prevented. Thus, the photoelectric conversion film 512c composed of the organic photoconductor is preferred particularly in the ISS type radiation detector 66.

The organic photoconductor in the photoelectric conversion film 512c preferably has an absorption peak wavelength closer to the emission peak wavelength of the scintillator 500 to absorb the visible light from the scintillator 500 more efficiently. It is ideal that the absorption peak wavelength of the organic photoconductor is equal to the emission peak wavelength of the scintillator 500. In a case where the difference between the peak wavelengths is small enough, the organic photoconductor can satisfactorily absorb the visible light from the scintillator 500. Specifically, the difference between the absorption peak wavelength of the organic photoconductor and the emission peak wavelength of the scintillator 500 under the radiation 16 is preferably 10 nm or less, more preferably 5 nm or less.

Such organic photoconductors satisfying the above requirement include quinacridone-based organic compounds and phthalocyanine-based organic compounds. For example, quinacridone has an absorption peak wavelength of 560 nm in the visible range. Therefore, in a case where the quinacridone is used as the organic photoconductor and CsI:Tl is used as the material of the scintillator 500, the difference between the above peak wavelengths can be 5 nm or less, whereby the amount of the electric charges generated in the photoelectric conversion film 512c can be substantially maximized.

The photoelectric conversion film 512c applicable to the radiation detector 66 will be described more specifically below.

In the radiation detector 66, an electromagnetic wave absorption/photoelectric conversion region may be formed by the upper and lower electrodes 512b and 512a and an organic layer containing the photoelectric conversion film 512c sandwiched between the upper and lower electrodes 512b and 512a. Specifically, the organic layer may be formed by stacking or combining an electromagnetic wave absorption component, a photoelectric conversion component, an electron transport component, a hole transport component, an electron blocking component, a hole blocking component, a crystallization preventing component, an electrode, an interlayer contact improving component, etc.

The organic layer preferably contains an organic p-type or n-type compound. The organic p-type semiconductor (compound) is an organic donor semiconductor (compound) typified by an organic hole transport compound, which has an electron donating property. More specifically, in a case where two organic compounds are used in contact with each other, the organic donor compound is one compound having a lower ionization potential. Thus, any organic compounds having the electron donating property can be used as the organic donor compound. The organic n-type semiconductor (compound) is an organic acceptor semiconductor (compound) typified by an organic electron transport compound, which has an electron accepting property. More specifically, in a case where two organic compounds are used in contact with each other, the organic acceptor compound is one compound having a higher electron affinity. Thus, any organic compounds having the electron accepting property can be used as the organic acceptor compound.

Compounds usable as the organic p-type and n-type semiconductors and the structure of the photoelectric conversion film 512c are described in detail in Japanese Laid-Open Patent Publication No. 2009-032854, and therefore explanations thereof are omitted.

Each of the photoelectric transducers 512 contains at least the upper electrode 512b, the lower electrode 512a, and the photoelectric conversion film 512c. Further, the photoelectric transducer 512 preferably contains at least one of an electron blocking film and a hole blocking film, and more preferably contains the both, to prevent dark current increase.

The electron blocking film may be disposed between the upper electrode 512b and the photoelectric conversion film 512c. In a case where a bias voltage is applied between the upper and lower electrodes 512b and 512a, the electron blocking film can prevent electron injection from the upper electrode 512b into the photoelectric conversion film 512c, and thus can prevent the dark current increase. The electron blocking film may be composed of an organic electron donating material. The material of the electron blocking film may be practically selected depending on the material of the adjacent electrode and the material of photoelectric conversion film 512c, etc. It is preferred that the material of the electron blocking film has an electron affinity (Ea) larger by 1.3 eV or more than the work function (Wf) of the material of the adjacent electrode and has an ionization potential (Ip) equal to or smaller than that of the material of the adjacent photoelectric conversion film 512c. Materials usable as the organic electron donating material are described in detail in Japanese Laid-Open Patent Publication No. 2009-032854, and therefore such materials will not be described in detail below.

The thickness of the electron blocking film is preferably 10 to 200 nm, more preferably 30 to 150 nm, particularly preferably 50 to 100 nm, from the viewpoints of reliably achieving the dark current reducing effect and preventing the photoelectric conversion efficiency of the photoelectric transducer 512 from being reduced.

The hole blocking film may be disposed between the photoelectric conversion film 512c and the lower electrode 512a. In a case where the bias voltage is applied between the upper and lower electrodes 512b and 512a, the hole blocking film can prevent hole injection from the lower electrode 512a into the photoelectric conversion film 512c, and thus can prevent the dark current increase. The hole blocking film may be composed of an organic electron accepting material. The material of the hole blocking film may be practically selected depending on the material of the adjacent electrode and the material of the adjacent photoelectric conversion film 512c, etc. It is preferred that the material of the hole blocking film has an ionization potential (Ip) larger by 1.3 eV or more than the work function (Wf) of the material of the adjacent electrode and has an electron affinity (Ea) equal to or larger than that of the material of the adjacent photoelectric conversion film 512c. Materials usable as the organic electron accepting material are described in detail in Japanese Laid-Open Patent Publication No. 2009-032854, and therefore such materials will not be described in detail below.

The thickness of the hole blocking film is preferably 10 to 200 nm, more preferably 30 to 150 nm, particularly preferably 50 to 100 nm, from the viewpoints of reliably achieving the dark current reducing effect and preventing the photoelectric conversion efficiency of the photoelectric transducer 512 from being reduced.

In a case where the bias voltage is provided such that, among the electric charges generated in the photoelectric conversion film 512c, the holes are transferred to the lower electrode 512a and the electrons are transferred to the upper electrode 512b, the positions of the electron blocking film and the hole blocking film may be reversed. It is not essential to form both of the electron blocking film and the hole blocking film. A certain level the dark current reducing effect can be achieved by forming one of the films.

The TFT 518 in the TFT layer 510 contains a stack of a gate electrode, a gate insulating film, and an active layer (channel layer). A source electrode and a drain electrode are disposed on the active layer at a predetermined distance. The active layer may be composed of an amorphous silicon, an amorphous oxide, an organic semiconductor material, a carbon nanotube, or the like, although the material of the active layer is not limited thereto.

For example, the amorphous oxide for the active layer is preferably an oxide containing at least one of In, Ga, and Zn (such as In—O oxide), more preferably an oxide containing at least two of In, Ga, and Zn (such as In—Zn—O, In—Ga—O, or Ga—Zn—O oxide), particularly preferably an oxide containing all of In, Ga, and Zn. The amorphous In—Ga—Zn—O oxide is preferably an amorphous oxide having a composition of $InGaO_3(ZnO)_m$ (wherein m is a natural number of less than 6) in a crystalline state, particularly preferably $InGaZnO_4$. It should be noted that the amorphous oxide for the active layer is not limited to such oxides.

The organic semiconductor materials for the active layer include, but not limited to, phthalocyanine compounds, pentacene, and vanadyl phthalocyanine. The structures of the phthalocyanine compounds are described in detail in Japanese Laid-Open Patent Publication No. 2009-212389, and therefore the structures will not be described below.

In a case where the active layer of the TFT 518 is composed of one of the amorphous oxides, the organic semiconductor materials, the carbon nanotubes, and the like, the active layer does not absorb the radiation 16 such as X-ray or absorbs only an extremely small amount of the radiation 16, and thereby can effectively reduce noise generation in the radiation detection part 502.

In a case where the active layer is composed of the carbon nanotube, the TFT 518 can have a high switching speed and a lowered visible light absorption. However, in a case where the active layer is composed of the carbon nanotube, the performance of the TFT 518 could be degraded significantly by trace metal impurities mixed with the active layer. Therefore, the carbon nanotube for the active layer has to be isolated and extracted by centrifugal separation or the like to have a high purity.

Both of the organic photoconductor and the organic semiconductor material can be used for forming a flexible film. Therefore, in the case of using the combination of the photoelectric conversion film 512c composed of the organic photoconductor and the TFT 518 containing the active layer composed of the organic semiconductor material, it is not necessary to increase the rigidity of the radiation detection part 502, to which a load is applied due to the body weight of the subject 14.

The insulative substrate 508 may be made of a material having a light transmittability and a low absorbability with respect to the radiation 16. Both of the amorphous oxide for the active layer in the TFT 518 and the organic photoconductor for the photoelectric conversion film 512c in the photoelectric transducer 512 can be formed into a film at low temperature. Therefore, the insulative substrate 508 is not limited to a highly heat-resistant substrate such as a semiconductor substrate, a quartz substrate, or a glass substrate, and may contain a flexible synthetic resin, an aramid, or a bionanofiber. Specifically, the insulative substrate 508 may be a flexible substrate of a polyester (such as a polyethylene terephthalate, a polybutylene phthalate, or a polyethylene naphthalate), a polystyrene, a polycarbonate, a polyethersulfone, a polyarylate, a polyimide, a polycycloolefin, a norbornene resin, a poly(chlorotrifluoroethylene), or the like. In the case of using the flexible synthetic resin substrate, the radiation detector 66 can be made lighter and easier to carry around. The insulative substrate 508 may have an insulating layer for maintaining the insulation property, a gas barrier layer for preventing penetration of moisture and oxygen, an undercoat layer for improving the flatness or the adhesion to the electrode, etc.

The aramid can undergo a process at a high temperature of 200° C. or higher. Therefore, in the case of using the aramid, a transparent electrode material can be hardened at a high temperature to lower the resistance, and a driver IC can be automatically mounted using a solder reflow process. Furthermore, the aramid has a thermal expansion coefficient close to those of ITO and glass, whereby the insulative substrate 508 containing the aramid is less liable to warp and crack after fabrication thereof. In addition, the insulative substrate 508 of the aramid can be made thinner as compared with glass substrates and the like. The insulative substrate 508 may be formed by stacking the aramid on an ultrathin glass substrate.

The bionanofiber is prepared by combining a transparent resin with a cellulose microfibril bundle (bacteria cellulose) produced by bacteria (acetic acid bacteria, Acetobacter Xylinum). The cellulose microfibril bundle has a width of 50 nm, which is 1/10 of the visible light wavelength, and exhibits a high strength, a high elasticity, and a low thermal expansion. The bionanofiber can be produced with a light transmittance of about 90% at a wavelength of 500 nm even at a fibril content of 60% to 70% by impregnating the bacteria cellulose with the transparent resin such as an acrylic resin or an epoxy resin and then hardening the resin. The bionanofiber has a low thermal expansion coefficient (3 to 7 ppm) comparable to a silicon crystal, a high strength (460 MPa) comparable to a steel, a high elasticity (30 GPa), and a high flexibility, whereby the insulative substrate 508 of the bionanofiber can be made thinner as compared with glass substrates and the like.

In a case where a glass substrate is used as the insulative substrate 508, the entire radiation detection part 502 (TFT substrate) has a thickness of e.g. about 0.7 mm. In the fourth modification, the thin light-transmittable substrate composed of the synthetic resin is used as the insulative substrate 508 to make the electronic cassette 20 thinner. Therefore, the entire radiation detection part 502 can have a small thickness of e.g. about 0.1 mm and can be flexible. In a case where the radiation detection part 502 is flexible, the electronic cassette 20 can exhibit an improved impact resistance and can be prevented from being broken due to the external shock. In a case where the insulative substrate 508 is composed of the material having the low radiation 16 absorbability (such as the plastic resin, the aramid, or the bionanofiber), the insulative substrate 508 absorbs only a small amount of the radiation 16. Therefore, even if the radiation 16 is transmitted through the radiation detection part 502 in the ISS type structure, the deterioration of the radiation 16 sensitivity can be prevented.

It is not essential to use the synthetic resin substrate as the insulative substrate 508 in the electronic cassette 20. The insulative substrate 508 may be composed of another material such as a glass although the other material may make the electronic cassette 20 thicker.

In the radiation detection part 502 (TFT substrate), the planarization layer 514 for planarizing the radiation detection part 502 is disposed remotely from the source of the radiation 16 (close to the scintillator 500).

In the fourth modification, the radiation detector 66 may be as follows.

(1) The photoelectric transducers 512 including the PDs may contain the organic photoconductor, and the TFT layer 510 may contain CMOS sensors. In this case, since only the PDs are made of an organic material, the TFT layer 510 containing the CMOS sensors may be inflexible. The photoelectric transducers 512 containing the organic photoconductor and the CMOS sensors are described in detail in Japanese Laid-Open Patent Publication No. 2009-212377, and therefore explanations thereof are herein omitted.

(2) The photoelectric transducers 512 including the PDs may contain the organic photoconductor, and the TFT layer 510 may be a flexible layer using CMOS circuits with TFTs composed of an organic material. In this case, the CMOS circuits may contain pentacene as an organic p-type semiconductor material, and may contain fluorinated copper phthalocyanine ($F_{16}CuPc$) as an organic n-type semiconductor material. In this manner, the TFT layer 510 can be a flexible layer having a smaller bend radius, and the gate insulating film can be significantly thinned to lower the drive voltage. Furthermore, the gate insulating film, the semiconductor, and the electrodes can be fabricated at a room temperature or a temperature of 100° C. or lower. In addition, the CMOS circuits can be fabricated directly on the flexible insulative substrate 508. The TFTs composed of the organic material can be microfabricated using a fabrication process according to a scaling law. The insulative substrate 508 can be produced as a flat substrate by spin-coating a thin polyimide substrate with a polyimide precursor and then heating the applied polyimide precursor to convert the same into polyimide.

(3) The PDs and the TFTs may contain crystalline Si and may be disposed on the insulative substrate 508 containing a resin by a fluidic self-assembly process. In the fluidic self-assembly process, a plurality of device blocks on the order of microns are placed at designated positions on a substrate. In this case, the PDs and the TFTs (corresponding to the device blocks on the order of microns) are prefabricated on another substrate, separated from the substrate, and statistically spread and positioned in a liquid on the insulative substrate 508 (corresponding to a target substrate). The insulative substrate 508 is preliminarily processed to adapt itself to the device blocks, so that the device blocks can be selectively placed on the insulative substrate 508. Accordingly, the optimum device blocks (the PDs and the TFTs) composed of the optimum material can be integrated on the optimum substrate (the insulative substrate 508). Thus, it is possible to integrate the PDs and the TFTs into the non-crystalline insulative substrate 508 (the resin substrate).

[Other Constitution Examples of the Embodiment]

The electronic cassette 20 of this embodiment is not limited to the above descriptions, and may have the following features. The following features may be used in combination with the above structures.

The air-bags 240 and 274 are described above as a specific example of the contact mechanism for contacting and separating the scintillator 150 and the radiation conversion panel 64. The contact mechanism is not limited to the specific example, and may have any structure as long as the scintillator 150 and the radiation conversion panel 64 can be dynamically brought into contact with and separated from each other by using the mechanism.

In the above embodiment and the first to third modifications, the inert gas generated in the inflator 120 is supplied to the air-bag 240 or 274, whereby the air-bag 240 or 274 is inflated. Alternatively, an air gas cylinder for externally supplying air may be mounted on or connected to the electronic cassette 20. In this case, a valve of the air gas cylinder is opened and closed, and the air is supplied from the air gas cylinder to the air-bag 240 or 274, whereby the air-bag 240 or 274 is inflated. Alternatively, a compressed air may be supplied from an air pump (compressor) to the air-bag 240 or 274, to inflate the air-bag 240 or 274. In the examples, in the step of deflating the air-bag 240 or 274, the air in the air-bag 240 or 274 may be discharged from a hole (not shown) or evacuated using an air pump.

In the drawings according to the above embodiment and the first to third modifications, the scintillator 150 and the radiation conversion panel 64 are completely separated from each other (in the non-contact states). The above embodiment and the first to third modifications are not limited to the drawings. The scintillator 150 and the radiation conversion panel 64 may be in contact with each other even if the contact control by the above-described contact mechanism is stopped, as long as the contact pressure is approximately zero or lower than the pressure observed in the process of pressing the scintillator 150 and the radiation conversion panel 64 against each other. In this case, though the scintillator 150 and the radiation conversion panel 64 cannot be completely separated from each other, the above-described effects can be achieved by stopping the contact control of the contact mechanism.

In the above embodiment and the first to third modifications, before the process of capturing the image of the subject 14, the scintillator 150 and the radiation conversion panel 64 may be brought into contact with (pressed against) each other by the contact mechanism based on the order information. After the process of capturing the image of the subject 14, the scintillator 150 and the radiation conversion panel 64 may be separated from each other, or the contact pressure between the scintillator 150 and the radiation conversion panel 64 may be lowered. Thus, the scintillator 150 and the radiation conversion panel 64 may be pressed against each other only in the image capturing process, in which the electronic cassette 20 is not likely to be subjected to the external shock. Therefore, also in this case, the above-described effects relevant to the contact control can be achieved.

It is to be understood that the present invention is not limited to the above embodiment, and various changes and modifications may be made therein without departing from the scope of the invention.

The invention claimed is:

1. A radiographic image capturing apparatus comprising a radiation detector having a scintillator for converting a radiation into a visible light and a radiation conversion panel for converting the visible light into an electric signal,
   wherein the scintillator contains columnar crystals for converting the radiation into the visible light,
   the columnar crystals extend in non-parallel with the radiation conversion panel,
   the scintillator has a convex surface facing the radiation conversion panel,
   the distal end portions of the columnar crystals are disposed on the convex surface, and
   the distal end portions of the columnar crystals are capable of being brought into contact with the radiation conversion panel.

2. The radiographic image capturing apparatus according to claim 1, wherein the radiation detector further has a buffer layer permeable to the visible light between the scintillator and the radiation conversion panel,
   the buffer layer has a first surface facing the scintillator and a second surface facing the radiation conversion panel,
   the first surface is capable of being brought into contact with the distal end portions of the columnar crystals, and
   the second surface is capable of being brought into contact with the radiation conversion panel.

3. The radiographic image capturing apparatus according to claim 2, wherein the convex surface of the scintillator is convexly curved and protruded toward the radiation conversion panel, and
   the first surface of the buffer layer is curved along the convex surface of the scintillator and is brought into contact with the distal end portions of the columnar crystals.

4. The radiographic image capturing apparatus according to claim 2, wherein the convex surface of the scintillator is tapered toward the radiation conversion panel,
   a center of the convex surface is approximately parallel to the radiation conversion panel, and
   the buffer layer is brought into contact with the center of the convex surface.

5. The radiographic image capturing apparatus according to claim 4, wherein a light shielding layer is disposed on a tapered portion of the convex surface of the scintillator to shield the visible light emitted from the distal end portions of the columnar crystals in the tapered portion.

6. The radiographic image capturing apparatus according to claim 2, wherein the buffer layer is a flexible plastic sheet.

7. The radiographic image capturing apparatus according to claim 6, wherein the buffer layer has a thickness of less than 50 μm.

8. The radiographic image capturing apparatus according to claim 7, wherein the buffer layer has a thickness of less than 30 μm.

9. The radiographic image capturing apparatus according to claim 7, wherein the buffer layer is a transparent sheet permeable to the visible light selected from silicone rubber films, polyimide films, polyarylate films, biaxially-oriented polystyrene films, and aramid films.

10. The radiographic image capturing apparatus according to claim 2, wherein a surface of the radiation conversion panel, which is brought into contact with the second surface of the buffer layer, is planarized with a tetrafluoroethylene resin film.

11. The radiographic image capturing apparatus according to claim 2, wherein the columnar crystals are cesium iodide crystals and are sealed by a protective moisture-proof material.

12. The radiographic image capturing apparatus according to claim 11, wherein the bottoms of the columnar crystals are disposed on a reflective film for reflecting the visible light converted from the radiation by the columnar crystals toward the buffer layer or a support board for supporting the scintillator and reflecting the visible light toward the buffer layer, the columnar crystals being vapor-deposited on the support board.

13. The radiographic image capturing apparatus according to claim 12, wherein the reflective film or the support board acts to seal the columnar crystals and has a moisture-proof property.

14. The radiographic image capturing apparatus according to claim 1, wherein the radiation conversion panel contains a flexible plastic sheet or a flexible thin glass sheet.

15. The radiographic image capturing apparatus according to claim 1, further comprising an image correction device for correcting a radiographic image corresponding to the electric signal read from the radiation conversion panel depending on the shape of the convex surface of the scintillator.

16. The radiographic image capturing apparatus according to claim 1, further comprising a contact mechanism for bringing the distal end portions of the columnar crystals into contact with the radiation conversion panel along the extending direction of the columnar crystals.

17. The radiographic image capturing apparatus according to claim 16, wherein the contact mechanism acts to bring the distal end portions of the columnar crystals into contact with the radiation conversion panel at least when the radiation is emitted to the radiation detector.

18. The radiographic image capturing apparatus according to claim 17, further comprising a transfer detector and a contact control device, wherein the transfer detector detects transfer of the radiographic image capturing apparatus,
   the contact control device controls the contact mechanism to bring the distal end portions of the columnar crystals into contact with the radiation conversion panel when the radiation is emitted to the radiation detector, and
   the contact control device controls the contact mechanism to stop contact control between the distal end portions of the columnar crystals and the radiation conversion panel in a case where a physical quantity relevant to the transfer of the radiographic image capturing apparatus detected by the transfer detector becomes larger than a predetermined threshold value.

19. The radiographic image capturing apparatus according to claim 18, wherein the contact control device controls the contact mechanism to bring the distal end portions of the columnar crystals into contact with the radiation conversion panel when a radiation source for emitting the radiation makes a preparation of the emission.

20. The radiographic image capturing apparatus according to claim 18, wherein the contact mechanism is an air-bag that is inflated and deflated along the extending direction of the columnar crystals to control the contact between the distal end portions of the columnar crystals and the radiation conversion panel, and the radiographic image capturing apparatus further comprises an inflator for supplying an inert gas to the air-bag to inflate the air-bag along the extending direction of the columnar crystals.

* * * * *